US012226235B2

(12) United States Patent
Rubinstein et al.

(10) Patent No.: US 12,226,235 B2
(45) Date of Patent: *Feb. 18, 2025

(54) APPARATUS AND METHOD FOR HEARTBEAT CLASSIFICATION BASED ON TIME SEQUENCE AND MORPHOLOGY OF INTRACARDIAC AND BODY SURFACE ELECTROCARDIOGRAM (ECG) SIGNALS

(71) Applicant: Biosense Webster (Israel) Ltd., Yokneam (IL)

(72) Inventors: Vladimir Rubinstein, Haifa (IL); Meir Bar-Tal, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 350 days.

This patent is subject to a terminal disclaimer.

(21) Appl. No.: 17/712,439

(22) Filed: Apr. 4, 2022

(65) Prior Publication Data

US 2022/0249030 A1   Aug. 11, 2022

Related U.S. Application Data

(63) Continuation of application No. 16/206,445, filed on Nov. 30, 2018, now Pat. No. 11,389,116.
(Continued)

(51) Int. Cl.
*A61B 5/00* (2006.01)
*A61B 5/287* (2021.01)
(Continued)

(52) U.S. Cl.
CPC ............ *A61B 5/7264* (2013.01); *A61B 5/287* (2021.01); *A61B 5/303* (2021.01); *A61B 5/327* (2021.01);
(Continued)

(58) Field of Classification Search
CPC .......... A61B 5/7264; A61B 5/327; A61B 5/35
(Continued)

(56) References Cited

U.S. PATENT DOCUMENTS

| 3,267,344 A | 8/1966 | McDaniel |
| 5,391,199 A | 2/1995 | Ben-Haim |

(Continued)

FOREIGN PATENT DOCUMENTS

| EP | 3130285 A1 | 2/2017 |
| EP | 3267344 A1 | 1/2018 |

(Continued)

OTHER PUBLICATIONS

Commerical webpage: https://www.biosensewebster.com/products/non-navigational/decapolar-deflectable-catheter.aspx accessed Sep. 26, 2018.
(Continued)

*Primary Examiner* — Nadia A Mahmood
(74) *Attorney, Agent, or Firm* — Volpe Koenig

(57) ABSTRACT

Classification of heartbeats based on intracardiac and body surface electrocardiogram (ECG) signals are provided. Intracardiac ECG (IC-ECG) signals and body surface ECG (BS-ECG) signals are processed to perform heartbeat classifications. A BS annotation of BS-ECG signals reflective of a sensed heartbeat is defined, the BS annotation including a BS annotation time value. IC annotations of IC-ECG signals which reflect atrial-activity or ventricular activity of the sensed heartbeat are also defined, each IC annotation including an IC annotation time value. The IC-ECG signals are discriminated as A-activity or V-activity and IC annotations are designated as IC-A annotations or IC-V annotations, respectively. A respective A/V time sequence comparison of IC annotations reflective of the sensed heartbeat is made with one or more time sequence templates for heartbeat
(Continued)

classification. Morphology comparisons of the BS-ECG oscillating signal segments reflective of the sensed heartbeat morphology templates for classification may also be made.

20 Claims, 15 Drawing Sheets

Related U.S. Application Data

(60) Provisional application No. 62/619,242, filed on Jan. 19, 2018.

(51) Int. Cl.
| | |
|---|---|
| *A61B 5/30* | (2021.01) |
| *A61B 5/327* | (2021.01) |
| *A61B 5/339* | (2021.01) |
| *A61B 5/35* | (2021.01) |
| *A61B 5/0245* | (2006.01) |
| *A61B 5/282* | (2021.01) |
| *A61B 5/316* | (2021.01) |
| *A61B 5/352* | (2021.01) |

(52) U.S. Cl.
CPC ................ *A61B 5/339* (2021.01); *A61B 5/35* (2021.01); *A61B 5/0245* (2013.01); *A61B 5/282* (2021.01); *A61B 5/316* (2021.01); *A61B 5/352* (2021.01); *A61B 5/6852* (2013.01); *A61B 5/7221* (2013.01); *A61B 5/7282* (2013.01); *A61B 2562/0209* (2013.01)

(58) Field of Classification Search
USPC ........................................................ 600/509
See application file for complete search history.

(56) References Cited

U.S. PATENT DOCUMENTS

| | | |
|---|---|---|
| 6,205,357 B1 | 3/2001 | Ideker et al. |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 8,700,136 B2 | 4/2014 | Rubinstein |
| 9,259,165 B2 | 2/2016 | Rubinstein et al. |
| 9,380,953 B2 | 7/2016 | Houben et al. |
| 10,323,423 B2 | 6/2019 | Locatell |
| 2002/0065455 A1 | 5/2002 | Ben-Haim et al. |
| 2003/0120150 A1 | 6/2003 | Govari |
| 2004/0059237 A1 | 3/2004 | Narayan et al. |
| 2004/0068178 A1 | 4/2004 | Govari |
| 2009/0099468 A1 | 4/2009 | Thiagalingam et al. |
| 2010/0268059 A1 | 10/2010 | Ryu et al. |
| 2011/0251505 A1 | 10/2011 | Narayan et al. |
| 2011/0319954 A1 | 12/2011 | Niazi et al. |
| 2013/0006131 A1 | 1/2013 | Narayan et al. |
| 2015/0073246 A1 | 3/2015 | Chmiel et al. |
| 2015/0208942 A1 | 7/2015 | Bar-Tal et al. |
| 2018/0008203 A1 | 1/2018 | Iyun et al. |

FOREIGN PATENT DOCUMENTS

| | | |
|---|---|---|
| JP | 2003-169854 A | 6/2003 |
| WO | 199605768 A1 | 2/1996 |

OTHER PUBLICATIONS

Extended European Search Report dated Jun. 25, 2019 for the European Patent Application No. 19152468.5.
Japanese Office Action mailed Nov. 8, 2022 for Japanese Patent Application No. 2019-006648.

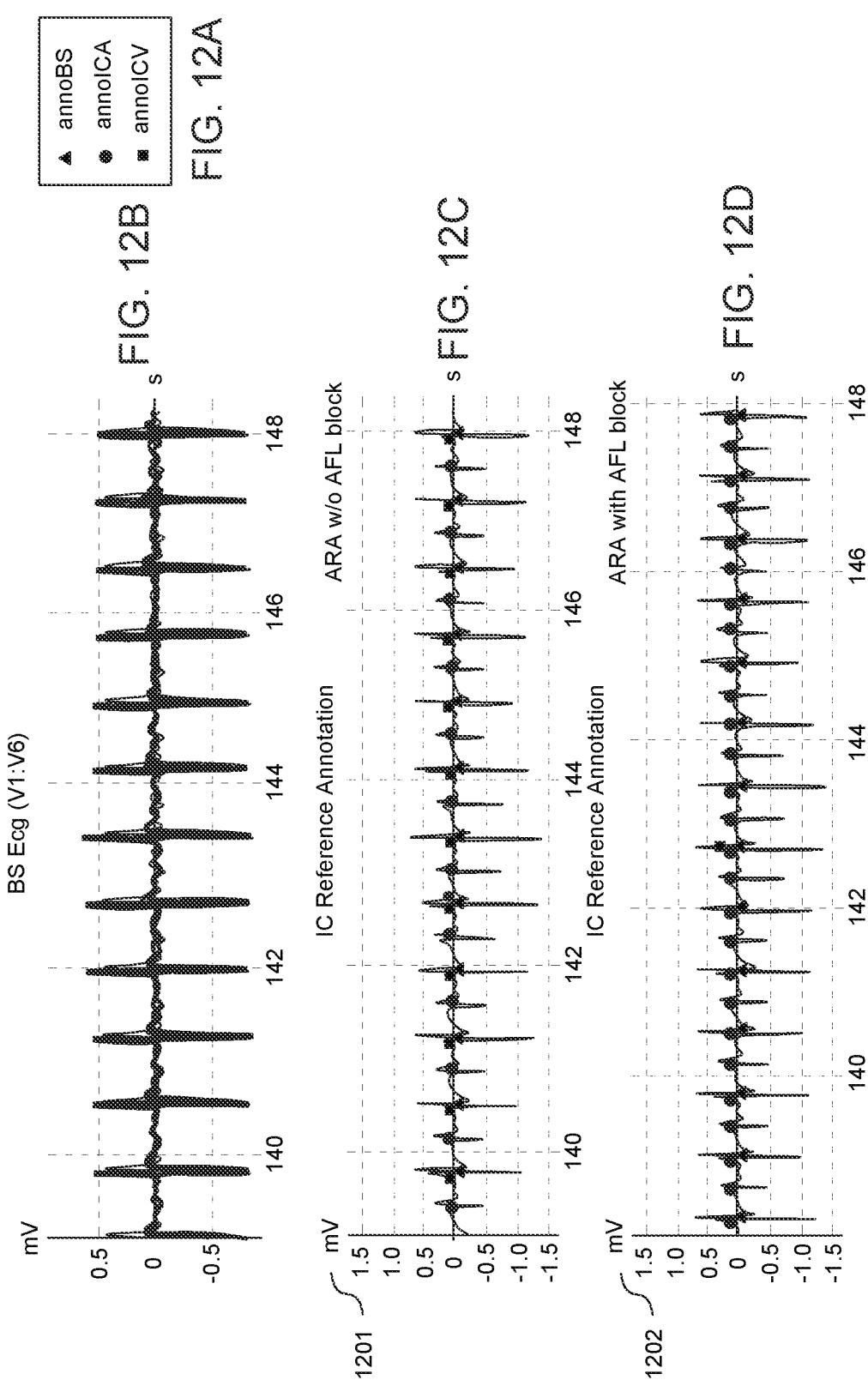

APPARATUS AND METHOD FOR HEARTBEAT CLASSIFICATION BASED ON TIME SEQUENCE AND MORPHOLOGY OF INTRACARDIAC AND BODY SURFACE ELECTROCARDIOGRAM (ECG) SIGNALS

CROSS REFERENCE TO RELATED APPLICATION

This application is a continuation of U.S. patent application Ser. No. 16/206,445, filed Nov. 30, 2018, which claims the benefit of Provisional Application No. 62/619,242 filed Jan. 19, 2018 which is incorporated herein by reference as if fully set forth.

SUMMARY

Medical apparatus and methods configured to classify heartbeats based on intracardiac and body surface electrocardiogram (ECG) signals are provided. An intracardiac catheter obtains multiple channels of intracardiac ECG (IC-ECG) signals via respective multiple electrodes when disposed within a heart within a body of a subject. A body surface ECG sensing device obtains multiple channels of body surface ECG (BS-ECG) signals via multiple electrodes when disposed on the body of the subject. A processor receives respective ECG signals from the intracardiac catheter and body surface ECG sensing device and processes the signals reflective of sensed heartbeats to perform heartbeat classifications.

An example apparatus includes a processor that defines a BS annotation of BS-ECG oscillating signal segments reflective of a sensed heartbeat of the subject, the BS annotation including a BS annotation time value relative to the sensed heartbeat. The processor performs a morphology comparison of the BS-ECG oscillating signal segments reflective of the sensed heartbeat with one or more morphology templates, where each morphology template is associated with a heartbeat classification. The sensed heartbeat is classified as corresponding to the associated heartbeat classification of a template for which the morphology comparison reflects a predetermined degree of morphology similarity.

The processor also defines IC annotations of IC-ECG oscillating signal segments for each channel which reflect atrial-activity (A-activity) or ventricular activity (V-activity) of the sensed heartbeat of the subject, each IC annotation including an IC annotation time value relative to the sensed heartbeat. The processor discriminates IC-ECG oscillating signal segments as A-activity or V-activity and designates IC annotations as IC-A annotations or IC-V annotations, respectively. The processor may then perform an Atrial time sequence comparison of IC-A annotations reflective of the sensed heartbeat with one or more Atrial time sequence templates, where each Atrial time sequence template is associated with an A-activity classification, and classify the sensed heartbeat as corresponding to the associated A-activity classification of a template for which the Atrial time sequence comparison reflects a predetermined degree of Atrial time sequence similarity. Alternatively, or in addition to, the processor may perform a Ventricular time sequence comparison of IC-V annotations reflective of the sensed heartbeat with one or more Ventricular time sequence templates, where each Ventricular time sequence template is associated with a V-activity classification, and classify the sensed heartbeat as corresponding to the associated V-activity classification of a template for which the Ventricular time sequence comparison reflects a predetermined degree of Ventricular time sequence similarity.

The medical apparatus preferably includes an output device coupled to the processor selectively output classifications of sensed heartbeats resulting from morphology and time sequence comparisons. The processor can also be configured to create a new morphology, Atrial time sequence or Ventricular time sequence template based upon a condition that a heartbeat classification is not made based on a respective comparison to existing morphology, Atrial time sequence or Ventricular time sequence templates.

In one example, the processor discriminates IC-ECG signal oscillating signal segments as A-activity or V-activity such that an IC-ECG oscillating signal segment is designated as V-activity upon a condition that the IC annotation time value relative to the sensed heartbeat is within a range of time values starting a predetermined amount before the BS annotation time value relative to the sensed heartbeat and ending a predetermined amount after the BS annotation time value relative to the sensed heartbeat and to otherwise designate the IC-ECG oscillating signal segment as A-activity. In such example, the processor may designate the IC-ECG oscillating signal segment as V-activity upon the condition that the IC annotation time value relative to the sensed heartbeat is within a range of time values starting at no less than 20 milliseconds before the BS annotation time value relative to the sensed heartbeat and ending no more than 80 milliseconds after the BS annotation time value relative to the sensed heartbeat.

In another example, the processor discriminates IC-ECG oscillating signal segments as A-activity or V-activity such that an IC-ECG oscillating signal segment is designated as A-activity or V-activity based upon morphology characteristics of the IC-ECG oscillating signal segment. In such example, the processor may discriminate IC-ECG oscillating signal segments as A-activity or V-activity such that an IC-ECG oscillating signal segment is designated as V-activity upon a condition that a combination of a slope and a width of a primary oscillation is less than a predetermined threshold and to otherwise designate the IC-ECG oscillating signal segment as A-activity.

In a further example, the processor is configured to designate the IC-ECG oscillating signal segments as A-activity upon the condition that atrial flutter is detected for the sensed heartbeat and a blanking window exists between successive IC-ECG oscillating signal segments for the sensed heartbeat.

An example processor may be configured to perform an Atrial time sequence comparison of IC-A annotations reflective of the sensed heartbeat with an Atrial time sequence template by calculating a time value difference between the IC annotation time value of the IC-A annotation for each channel of the sensed heartbeat and a respective template channel annotation time value and then determining that the predetermined degree of Atrial time sequence similarity occurs when the combination of the absolute value of the combined differences is no greater than a selected A-time threshold. Such an example processor can also be configured to perform a Ventricular time sequence comparison of IC-V annotations reflective of the sensed heartbeat with a Ventricular time sequence template by calculating a time value difference between the IC annotation time value of the IC-V annotation for each channel of the sensed heartbeat and a respective template channel annotation time value and then determining that the predetermined degree of Ventricular time sequence similarity occurs when the combination of the absolute value of the combined differences is no greater than a selected V-time threshold.

The apparatus may employ a monitor as an output device that is configured to selectively display ECG signal and heartbeat classification data of sensed heartbeats.

BRIEF DESCRIPTION OF THE DRAWINGS

A more detailed understanding can be had from the following description, given by way of example in conjunction with the accompanying drawings.

FIGS. 12A-D is a comparison of the results of classification methods; FIG. 12A being a legend, FIG. 12B a body scan (BS) graph, FIG. 12C an IntraCardiac (IC) graph without AFL mode method and FIG. 12D an IC graph with AFL mode method.

DETAILED DESCRIPTION

Figure 1A:
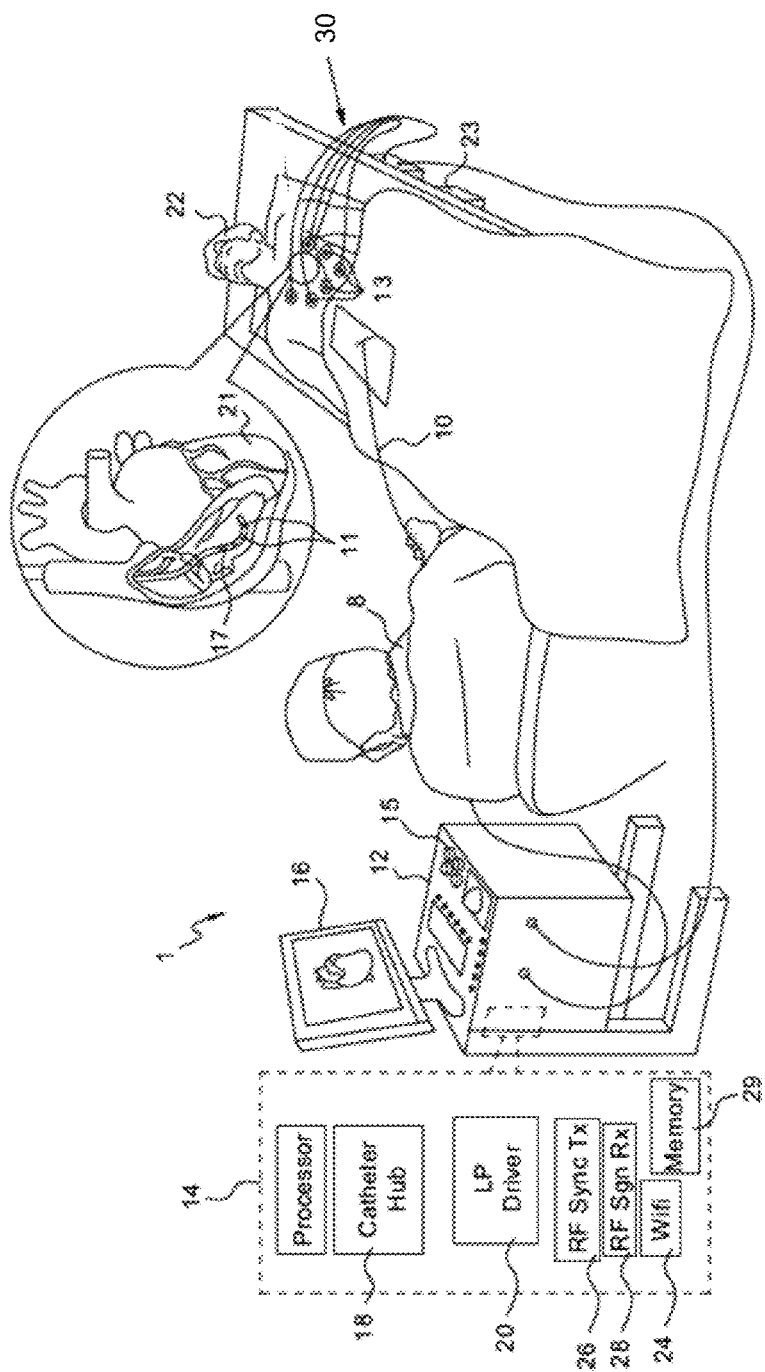
FIG. 1A is a schematic illustration of an electrocardiogram (ECG) analysis system, according to an embodiment of the present invention.

The normal sinus rhythm of heartbeats commences when the sinoatrial (SA) node in the heart initiates a depolarization wave over the atrial tissue resulting in atrial heart muscle contraction, pushing blood in the atria into the ventricles. After a delay of about 70 ms, a depolarization wave initiating in the atrioventricular (AV) node passes over the ventricular heart tissue resulting in a ventricular muscle contraction that pushes blood out of the ventricles. Preparation or "reset" for the next heartbeat occurs with repolarization waves in both the atria and ventricles. This electrical activity results in the classic ECG waveform morphology (e.g., P-wave, QRS-complex, T-wave) that can be detected using ECG body surface (BS) electrodes. Each heart beat is reflected as an oscillating segment in the BS-ECG signal.

The atrial and ventricular activation waves, produced by the SA node and passed through AV node, spread out over the heart muscle as a wave front with a spatially dependent propagation time. When using Intra-Cardiac electrodes to generate an ECG, i.e. IC-ECG, the IC-ECG signal includes oscillating segments reflecting respective atrial and ventricular activity of a heartbeat. For a normal heart beat, an atrial oscillating signal segment will be separate from and precede (in time) a ventricular oscillating signal segment. However, in some types of abnormal heart beats, oscillating signal segments reflecting atrial and ventricular oscillating signal segments will overlap in time.

Unstable heart activation causes the wave activation inside a heart chamber to change between heartbeats. Because activation activities may not always be constant, the likelihood that particular relevant activities will be missed by the physician is significant. Cardiac mapping, for example, creating a map of electrical potentials (a voltage map) of the wave propagation along the heart tissue or a map of arrival times (a local time activation (LAT) map) to various tissue located points may be used for detecting local heart tissue dysfunction Annotation of the ECG oscillating signal segments may be used to indicate a consistent timing in the heart cycle in order to create a reliable LAT map. Annotations refer to points of time on an electrogram that are considered to denote events of interest. A misclassified annotation can cause acquisition of false volume and false local activation timing into the map. The common practice is to place the reference catheter in a stable position in the coronary sinus (CS). Recording of the catheter's ECG at that position records both atrial and ventricular contractions which represent different timings of the heart cycle; because of the different timings, it is important to differentiate the atrial and ventricular contractions. The suggested methods presented herein assure A-V differentiation thus providing a reliable and consistent reference.

To assist the physician in finding relevant activities, an enhanced system to track and understand the different activation activities that occur during the mapping process is needed.

The present system provides enhanced understanding of unstable heart activation by focusing on the sequence of activity inside a catheter placed within some stable position (for example, a "CS catheter" placed within the coronary sinus (CS)). This information may be used to understand the source of the normal and/or abnormal heart activation.

CARTO™ electroanatomic mapping and navigation system produced by Biosense Webster, Inc. (Diamond Bar, California) uses a mapping catheter with a localization sensor in its tip to automatically and simultaneously acquire an electrogram and determine its three-dimensional coordinates.

A method of position sensing is implemented in the above-mentioned CARTO™ system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

The CARTO™ system also implements a method for cardiac mapping based upon determination and analysis of ECG signal annotations, which is described in detail in U.S. Pat. Nos. 8,700,136 and 9,259,165, whose disclosures are both incorporated herein by reference.

FIG. 1A is a schematic overview of the medical apparatus 1 in accordance with an example embodiment of the present invention. As shown in FIG. 1A, the medical apparatus 1 is configured inter alia to classify sensed beats of a heart 21 of a subject or patient 22 and includes one or more medical tools (e.g., mapping catheters, reference catheters, ablation catheters, etc.), such as intracardiac catheter 10, and a work station 12 having a processor 14, an associated display or monitor 16, a catheter hub 18, a location pad (LP) driver 20, Wi-Fi antenna 24, RF Sync Tx antenna 26 and RF Sync Rx antenna 28. The LP driver is coupled to a location pad (not shown) disposed beneath the patient 22. The intracardiac catheter 10 has an array of catheter sensors (e.g., electrodes) 11 at a distal end 17. Each sensor is configured to detect electrical activity (electrical signals) of an area of the heart 21 over time. In one embodiment, each electrode 11 is a metal ring on the surface of the intracardiac catheter 10. When an intracardiac electro-cardiogram (IC ECG) is performed, each electrode 11 detects the electrical activity of an area of the heart 21 with which it is in contact.

In one embodiment, the processor 14, e.g., a hardware unit ("PIU"), is configured to process the signals received from the sensors 11 to calculate ECG values with respect to the catheter tip. The processor 14 may be specialized processing hardware. The received data, e.g., ECG signals from the intracardiac catheter 10, may be processed by a reference annotation method, as discussed below. The processor 14 includes memory resources for organizing the received data.

The catheter hub 18 is configured to receive data from multiple sensors, which may include the sensors 11, for navigation. The LP driver 20 drives current, such as AC, to the location pad to enable field generators within the pad to generate magnetic fields which define a reference magnetic field for navigation of the catheter 10. The catheter hub 18 may be hard wired or include a Wi-Fi antenna 24 and an RF Sync Rx antenna 28, for receiving signals from the tools that are navigated. The LP driver 20 may be hard wired or include a Wi-Fi antenna 24 and an RF Sync Tx antenna 26 enabling the LP driver 20 to transmit current to the location pad.

The position and orientation of the distal end of the intracardiac catheter 10 may be ascertained by determining the position of a magnetic field locating sensor within its distal end 17. The intracardiac catheter 10 may be locatable with a non-ionizing field, such as an electromagnetic or acoustic field. The distal end 17 of the intracardiac catheter 10 may comprise a transmitting or receiving antenna (not shown) for the relevant field. Receiving or transmitting antennas for the non-ionizing field may be attached to the patient 22 for aiding navigation. A receiver or transmitter is connected to these antennas, and converts the received field waves into electrical locating or image signals.

The location pad may comprise coils (not shown), which are one type of magnetic transducer that may be used in embodiments of the present invention (see incorporated U.S. Pat. No. 6,618,612). A "magnetic transducer," in the context of the present patent application and in the claims, means a device that generates a magnetic field in response to an applied electrical current and/or outputs an electrical signal in response to an applied magnetic field.

The work station 12 can be detachably connected via an output connection to the display 16. The work station 12 is also detachably connected via an input connection to the catheter hub 18 to which one or more medical tools can be connected. The input and output connections may be hard-wired or Wi-Fi connections, or both. One or more tools, such as the intracardiac catheter 10, may be navigated through the patient's heart 21. Although the work station 12, the LP driver 20 and the catheter hub 18 are shown included together as a single component, they may all be separate components, or variously combined as fewer components.

In use, the intracardiac catheter 10 may be percutaneously inserted into the body of the subject 22 during a cardiac mapping procedure performed by a user 8. In the description herein the user 8 is assumed, by way of example, to be a physician or other medical professional. Body surface electrodes 13 of a body surface ECG sensing device 30 may be attached to the skin of subject 22. During a procedure, the subject 22 is preferably attached to a grounding electrode 23.

Figure 1B:
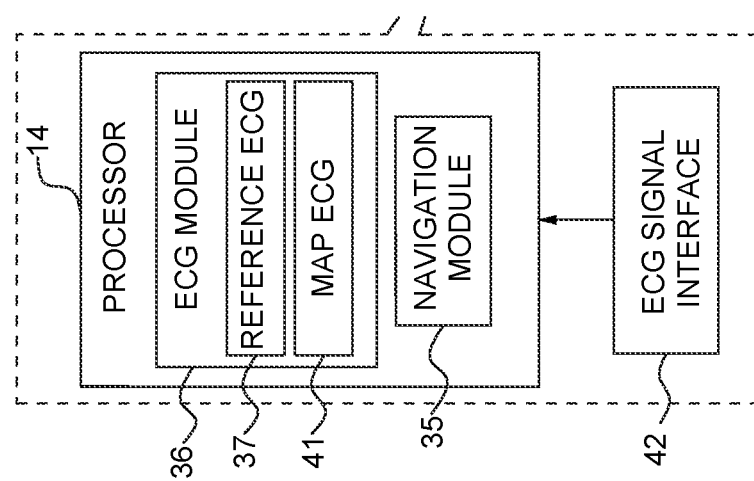
FIG. 1B is an example configuration of processing components of the by system shown in FIG. 1.

For simplicity and clarity, the following description, except where otherwise stated, assumes a medical procedure that senses electrical signals from the heart 21, using electrodes 11 disposed on the intracardiac catheter 10 and the electrodes 13 of the body surface ECG sensing device 30. As illustrated in FIG. 1B, the electrodes can be coupled to an ECG signal interface 42 which inputs the sensed electrical signals into the processor 14.

When the electrodes 11 contact the heart tissue and the electrodes 13 contact the subject's body, the processor 14 receives multiple electrical signals from the electrodes. For heartbeat classification, the intracardiac catheter 10 is positioned in a reference region of the heart, such as in the coronary sinus, and used to sense intracardiac (IC) ECG signals from the region while the electrodes 13 are used to sense body surface (BS) ECG signals.

The processor 14 is typically mounted in a console 12, which comprises operating controls 15. The controls 15 typically include a pointing device, such as a mouse or a trackball. A professional 8 can use the pointing device to interact with the processor 14. Results of the operations performed by processor 14 are presented to the user 8 on a display 16, which typically presents a graphic user interface to the operator, a visual representation of the ECG signals sensed by the electrodes 11 and 13.

FIG. 1B is an example configuration of the processor 14 which may be a general purpose processor configured with software or a special processor such as an application-specific integrated circuit (ASIC). The processor can be configured with a probe navigation module 35 and an ECG module 36, to respectively control the positioning of the intracardiac catheter 10 and the processing of the ECG signals. The ECG module 36 can include a reference ECG sub-module 37 and a map ECG sub-module 41, whose functions are described below. Software may be downloaded to the processor 14 in electronic form, over a network, for example, or it may, alternatively or additionally, be provided and/or stored on non-transitory tangible media, such as magnetic, optical, or electronic memory. The ECG signal interface 42 receives the ECG signals from Intracardiac (IC) electrodes 11 and the Body Surface (BS) electrodes and relays the signals to processor 14. ECG module 36 is configured to analyze the received ECG signals and may present the results of the analysis in a standard ECG format, typically a graphical representation moving with time, on display 16. For navigation, the signals from the Intracardiac (IC) electrodes 11 may be used as references with respect to signals from sensors of additional catheters as described in the U.S. Patents referenced above.

The probe navigation module 35 tracks sections of catheter 10 within subject 22. The navigation module typically tracks both the location and orientation of the distal end of the catheter 10 within the heart 21 of the subject 22. In some embodiments module 35 tracks other sections of the catheter or other tool. The navigation module 35 may use any method for tracking tools known in the art. For example, the navigation module 35 may operate magnetic field generators in the vicinity of the subject, so that magnetic fields from the field generators interact with tracking coils located in sections of the probe being tracked. The coils interacting with the magnetic fields generate signals which are transmitted to module 35, which analyzes the signals to determine a location and orientation of the coils. For simplicity such coils and field generators are not shown in FIG. 1A. The Carto® system produced by Biosense Webster, of Diamond Bar, Calif., uses such a tracking method.

Alternatively or additionally, the navigation module 35 may track the catheter 10 by measuring impedances between the ground electrode 23, the body surface (BS) electrodes 13 and the IC electrodes 11, as well as the impedances to other electrodes which may be located on the probe. The IC electrodes 11 and/or BS electrodes 13 may provide both ECG and tracking signals. The Carto3® system produced by Biosense Webster uses both magnetic field generators and impedance measurements for tracking.

Figure 2:
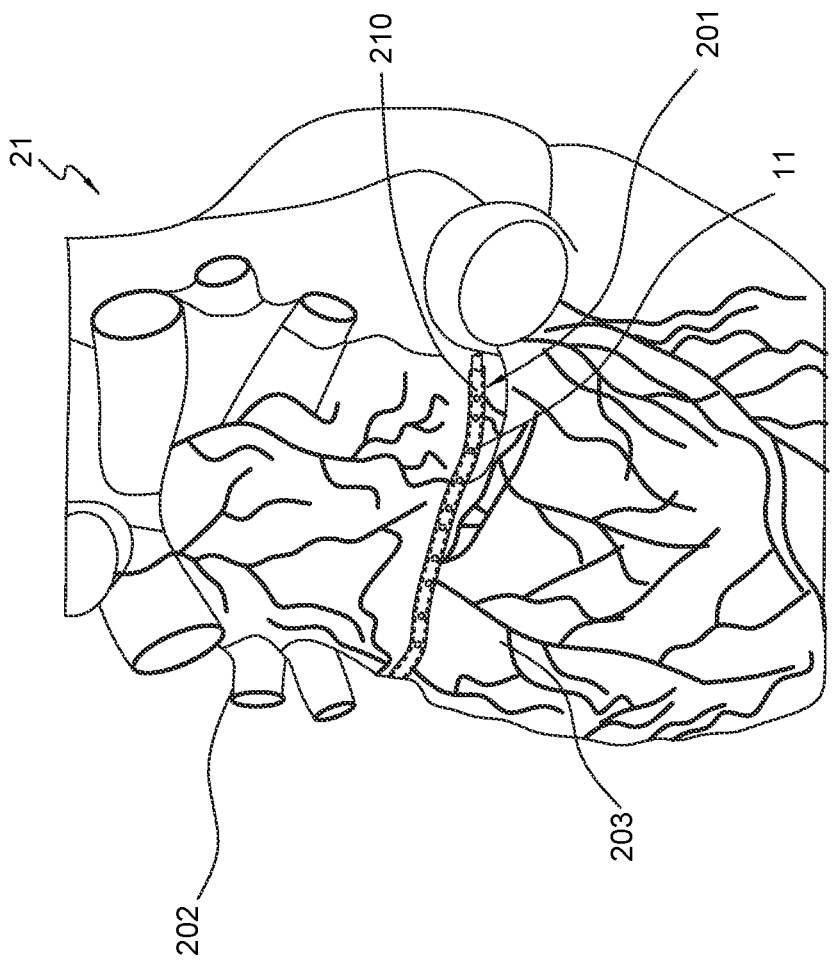
FIG. 2 is an example illustration of a catheterized heart organ.

FIG. 2 illustrates the example subject's heart 21 which includes a Coronary Sinus (CS) 201. The CS 201 separates the left atrium 202 from the left ventricle 203. The IC catheter 10 direction may be projected on the display 16 of the IC catheter 10 along with a time sequence. Heart activity propagation that is projected on the IC catheter can be used to generate a time sequence of ECG signal appearances in different electrodes. The directions can be from distal to proximal electrodes, from proximal to distal electrodes, or more complex patterns that may include electrodes of multiple catheters. Determining the direction can provide important information regarding source of the heart activation.

Decapolar catheters are typically used in the CS 201. For example, the IC catheter 10 may be a WEBSTER® Decapolar Deflcable Catheter comprising five pairs of evenly spaced electrode sensors 11. Other examples include WEBSTER® PentaRay® NAV or Navistar® Thermocool® catheters that may be used in addition to catheter 10 or as alternatives.

To visualize an activation wave on the heart 21, a reference point in time is needed, from beat to beat and for each anatomical position point taken during a mapping process. A physician can track time about the reference point. The coronary sinus provides an excellent reference point because it is positioned between the atrium and the ventricle, allowing the catheter 10 to closely monitor both atrial activity and ventricular activity. However, other locations can be used.

The sensed heart activity is advantageously used for mapping the different sections of the heart 21. When is mapping the atrium 202, atrial activity can be used as a reference. When mapping the ventricle 203, ventricular activity can be used as a reference.

Further, the CS is an optimal reference point because the time patterns of the CS activations can be helpful in atrial tachycardia (AT) mapping. The analysis of time patterns of CS activation provides a rapid stratification, or ordering, of most likely macro-reentrant ATs (MRATs), and the analysis also points toward the likely origin of focal ATs.

During a medical procedure to examine a patient's heart, CARTO™ system accumulates information as the physician 8 (or other medical practitioner) moves the catheter 10 or other tool within the patient's heart 21 from point to point and filters the data obtained from the catheter 10 or other tool for "relevant" data. For example, CARTO™ can calculate the time of a heartbeat cycle length, e.g., "beat-to-beat time", and this information can be used for analyzing the patient's heart behavior.

Enhanced understanding of heart activation requires more detailed information than provided by existing systems; for instance, filters that recognize activity and/or activation from more than one direction can provide enhanced understanding of heart activation. To overcome this deficiency, techniques to determine CS catheter 10 direction can be employed. Additionally, heartbeat classification may be employed to enhance mapping of the heart for use in further medical procedures.

Figure 3A:
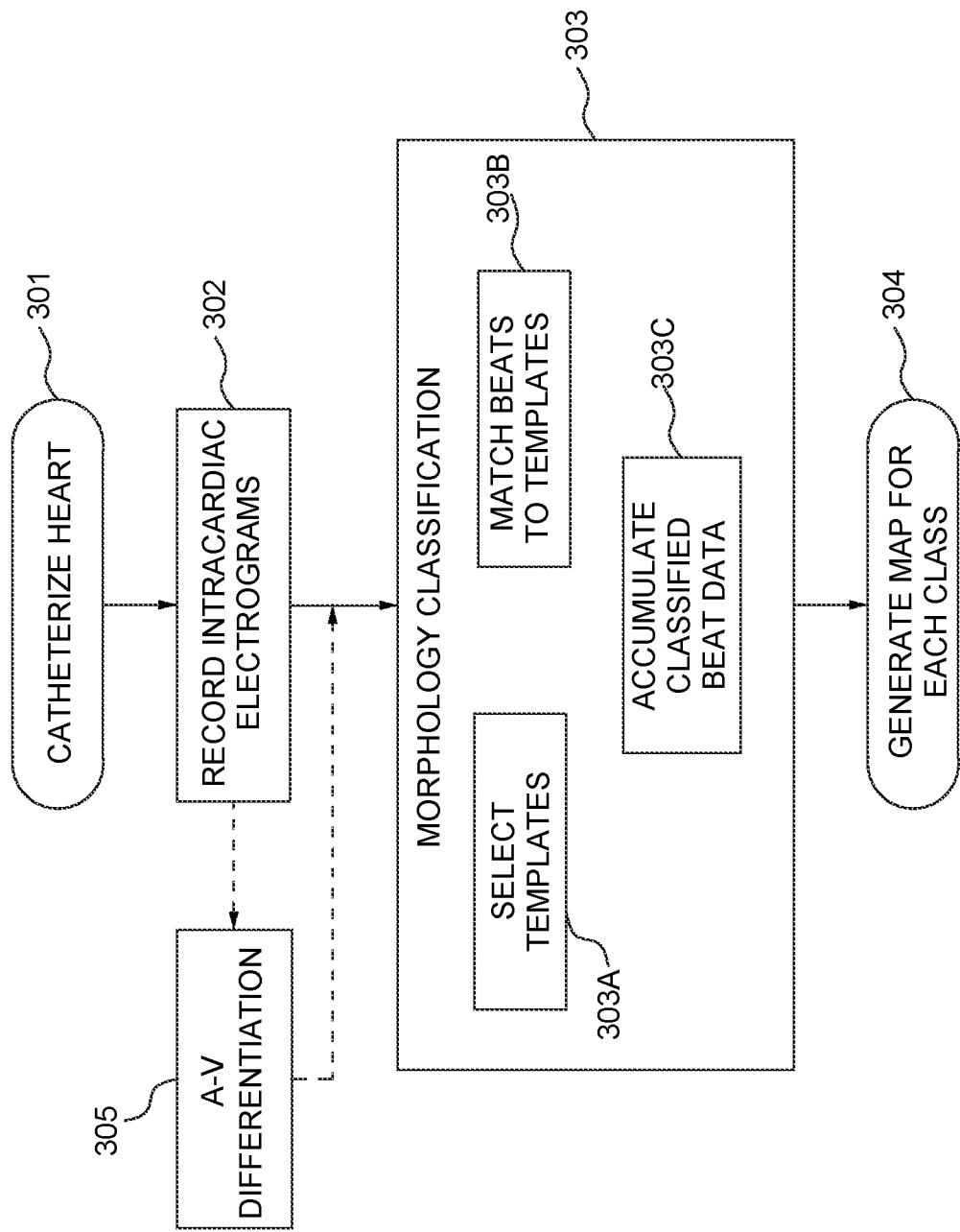
FIG. 3A is a flow diagram of a method to identify and classify various heart activations using morphology template comparison.

FIG. 3A is a flow diagram of an improved method for preparing electroanatomic maps of the heart adapted from commonly owned U.S. Patent Publication No. 2018/0008203, Automatic Creation of Multiple Electroanatomic Maps, which is incorporated by reference as if fully set forth, that include heartbeat classification using a morphological comparison of ECG heartbeat signals. The process steps are shown in a particular linear sequence. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At an initial step 301 the heart is catheterized with the electrodes of the catheter preferably placed in galvanic contact with the CS. Next, at step 302, intracardiac electrograms, i.e. sensed ECG signals, are recorded and oscillating ECG signal segments reflective of heart activity are annotated with the multiple electrodes of the catheter, each having a respective location, which can be determined using the position tracking capabilities of the medical apparatus depicted in FIG. 1.

The recordings may be obtained and processed concurrently. The electrograms may be recorded and data collected throughout a catheterization session as the catheter is navigated within the heart. Additionally or alternatively the data may be collected in a "hunting mode", wherein the catheter is stable in a location, and the operator awaits rhythm changes generally, or the appearance of a particular arrhythmia. The data may be collected using unipolar or bipolar electrode configurations.

Annotation of the intracardiac electrograms defines respective time value annotations of oscillating ECG signal segments and may be performed using the teachings of commonly assigned U.S. Patent Publication No. 20150073246, entitled Method for Mapping Ventricular/Atrial Premature Beats During Sinus Rhythm, U.S. Pat. No. 9,380,953, entitled Hybrid Bipolar/Unipolar Detection of Activation Wavefront, and U.S. Patent Publication No. 20150208942, entitled Double Bipolar Configuration for Atrial Fibrillation Annotation, which are herein incorporated by reference.

Next, heartbeat classification, step 303, using a morphological comparison of the shape of oscillating ECG signal segments is performed. The morphology comparison of oscillating signal segments reflective of the sensed heartbeat is conducted with respect to one or more morphology templates, where each morphology template is associated with a heartbeat classification. The sensed heartbeat is classified as corresponding to the associated heartbeat classification of a template for which the morphology comparison reflects a predetermined degree of morphology similarity.

As explained in detail in U.S. Patent Publication No. 2018/0008203, such morphology comparison may comprise a template selection step 303A, a template matching step 303B, in which the morphology of the intracardiac electrograms is automatically matched to the templates beat-by-beat, and a data accumulation step 303C. The templates are typically user defined, and may represent a pre-defined signal morphology based on an average heartbeat waveform of the patient, and/or signal estimation for an anomaly such as a fibrillation. Additional new templates may also be derived from the morphology of oscillating ECG signal segments of a sensed heartbeat when a heartbeat classification is not made based on a respective comparison to existing morphology, time sequence or combined template.

Following the classification and data accumulation, a functional electroanatomic map, e.g., an LAT map, is automatically generated, step 304. A detailed explanation of steps 301-304 for LAT map generation is provided in U.S. Patent Publication No. 2018/0008203.

Figure 5:
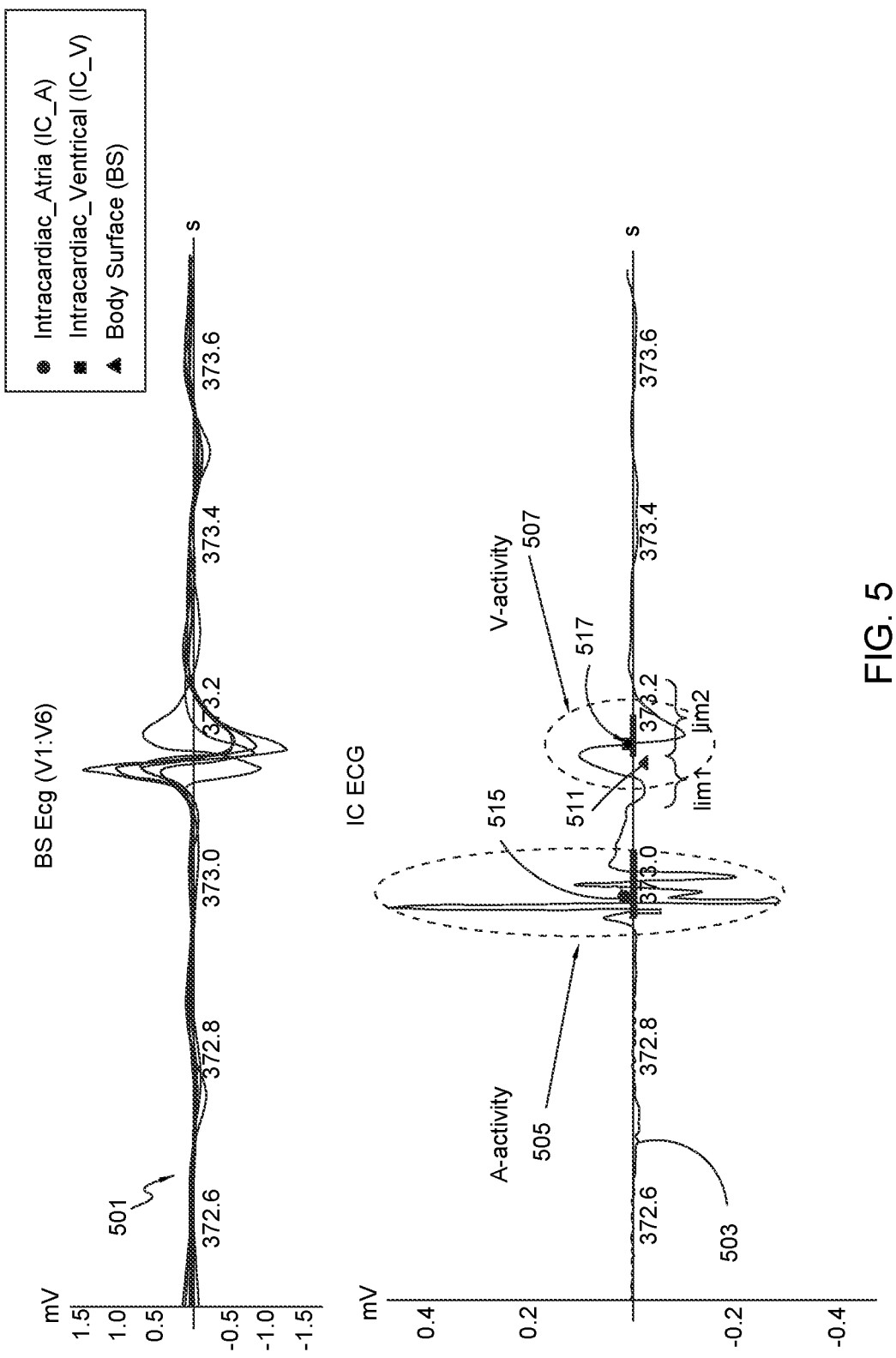
FIG. 5 is a graphic illustration of ECG signals of a sample "normal" sensed heartbeat comparing body source (BS) traces from BS electrodes to an intracardiac (IC) trace from an IC electrode of the same sensed heartbeat with annotation references noted.

Different information is reflected in the ECG signals sensed by the IC electrodes 11 and the BS electrodes 13. FIG. 5 is a graphic illustration of ECG signals of a typical normal sensed heartbeat comparing body source (BS) traces from BS electrodes 13 to an intracardiac (IC) trace from an IC electrode 11 of the same sensed heartbeat with annotation references noted. As illustrated in FIG. 5, traces 501 of BS-ECG signals each characteristically reflect a single oscillating signal segment for the sensed heartbeat. By comparison, the trace 503 of the IC-ECG signal characteristically reflects two oscillating signal segments for the sensed heartbeat; the first 505 corresponding to atrial activation activity (IC-A segment) and the second 507 corresponding to ventricular activation activity (IC-V segment).

Building upon the prior classification and mapping technique discussed above with respect to steps 301-304, an additional step 305 of atrial-ventricular differentiation of oscillating IC-ECG signal segments can be performed. Such differentiation may be made, for example, by a time sequence technique described with respect to FIGS. 4-6 below and/or a morphological technique described with respect to FIGS. 7-9 below.

In preparation of atrial-ventricular differentiation 305, in step 302, signals from each IC electrode are segmented and annotated to produce a time value annotation for each oscillating signal segment of each IC channel, each electrode defining a separate IC channel. However, an annotation of the collective BS channel signals for a sensed heartbeat can be advantageously employed in conducting the atrial-ventricular differentiation.

When atrial-ventricular differentiation 305 is employed in the method depicted in FIG. 3A, the IC-A signal segments and the IC-V signal segments can be processed in separate groups with the morphology classification being performed separately with respect to the IC-A signal segments and the IC-V signal segments. In such manner, the processed IC-A segments can be advantageously used in creating atrial mappings and the processed IC-V segments can be advantageously used in creating ventricular mappings. For implementation in the medical apparatus 1, typically the processor 14 is configured to perform steps 301-305.

Although morphology classification works well with BS-ECG signal segments, the inventors have recognized that heart beat classification on a time sequence comparison can be advantageously employed for heartbeat classification of IC-ECG signal segments.

Figure 3B:
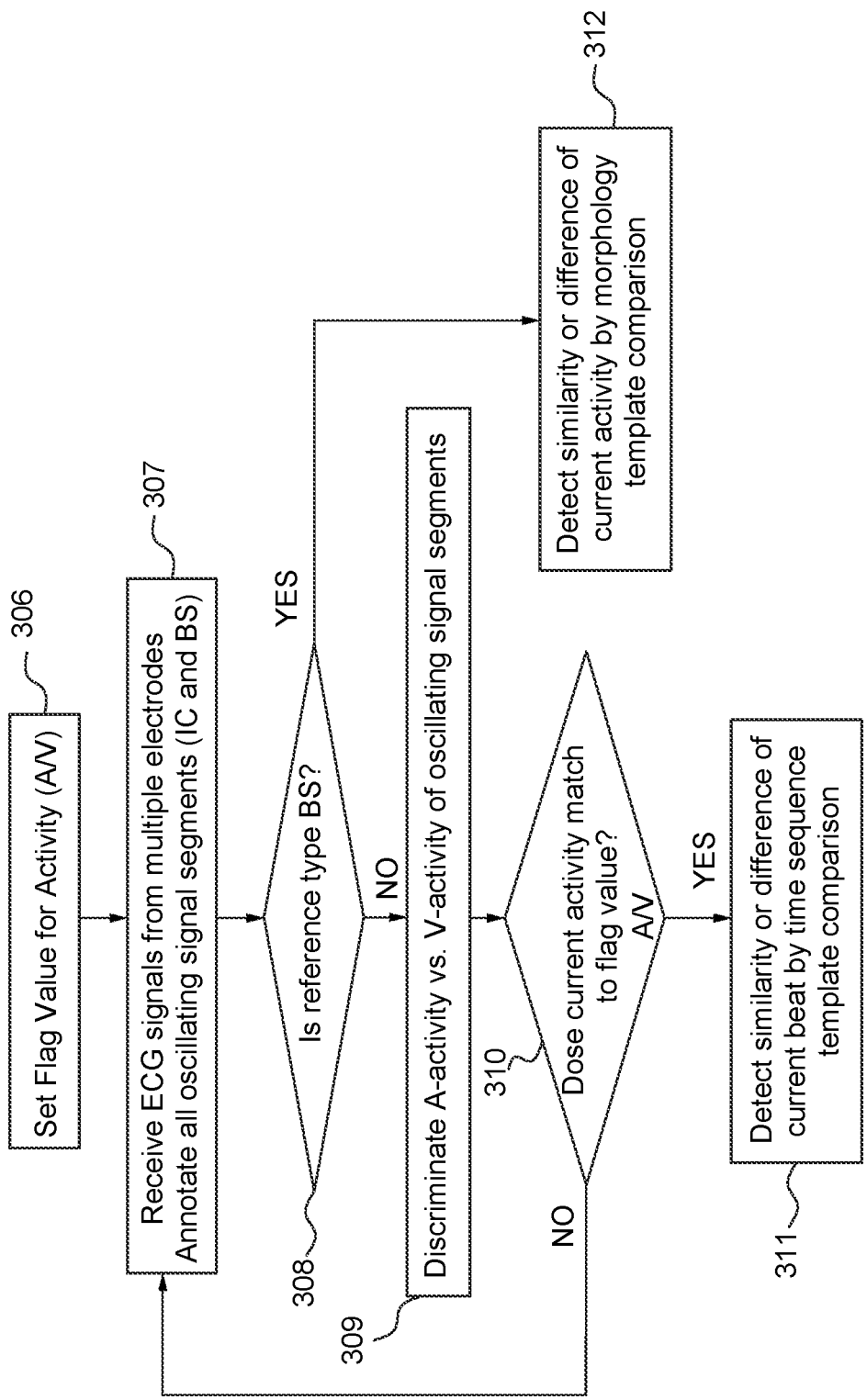
FIG. 3B is a flow diagram of a method to identify and classify various heart activations that includes time sequence comparison in accordance with the teachings of the present invention.

FIG. 3B is a flow diagram of a system of heartbeat classification of ECG signal segments that employs both morphology and time sequence comparisons. For implementation in the medical apparatus 1, typically the processor 14 is configured to perform the classification process.

For one example, in an initial step 306, a flag value can be set to define the activity source of an oscillating signal segment of interest, i.e. atrial ("A") or ventricular ("V"). The flag value is typically set by the user 8, but may be set automatically as part of a pre-configured program. For example, the Flag may first be set to "A" to accumulate data for an atrial mapping and the switched to "V" to reprocess the ECG signals to accumulate data for a ventricular mapping.

In step 307, ECG signals are received from multiple electrodes, such as from both the Intracardiac (IC) electrodes 11 and the body surface (BS) electrodes 13. The oscillating signal segments are processed and annotated to define annotations that include a time value relative to respective sensed heartbeats as described above in connection with Step 302 of FIG. 3A. Signals from each IC and BS electrode are segmented and annotated to produce a time value annotation for each oscillating signal segment of each IC and BS channel, each electrode defining a separate IC or BS channel. However, an annotation of the collective BS channel signals for a sensed heartbeat can be advantageously employed in conducting subsequent atrial-ventricular differentiation of the IC-ECG signal segments.

In step 308, a determination is made as to whether the annotated oscillating signal segment is from a BS-ECG signal originated from body surface (BS) electrodes 13 or not. If it is, the BS-ECG signal segment data is passed for collection and processing in a morphology comparison step 312. In step 312, the BS signal segments are analyzed to detect similarity or difference of a sensed heartbeat by morphology template comparison. This process can be conducted as explained above in step 303 of the process illustrated by FIG. 3A.

The non-BS signal segment data, i.e. the IC-ECG oscillating signal segment data, passes though the decision step 308 to an atrial-ventricular differentiation/discrimination step 309. The discrimination between A-activity versus V-activity can be made in various ways as referenced with respect to step 305 of the process illustrated by FIG. 3A. Such differentiation may be made using IC-ECG oscillating signal segment annotations, for example, by a time sequence technique described with respect to FIGS. 4-6 below and/or by using the IC-ECG oscillating signal segment shape in a morphological technique described with respect to FIGS. 7-9 below. In connection with the discrimination of the IC-ECG oscillating signal segments as A-activity or V-activity, the respective annotations of the IC-ECG segments are designated as IC-A annotations or IC-V annotations, In step 310, the IC-ECG oscillating signal segments are filtered based on the flag value set in step 306. Where the flag value is "A," the IC-ECG oscillating signal segment data reflecting Atrial activity is passed to step 311 for further processing, otherwise the IC-ECG oscillating signal segment data is returned to await processing when the flag value is set to "V." Where the flag value is "V," the IC-ECG oscillating signal segment data reflecting Ventricular activity is passed to step 311 for further processing, otherwise the IC-ECG oscillating signal segment data is returned to await processing when the flag value is set to "A."

In contrast to the morphology classification process of step 312 for the BS-ECG oscillating signal segment data, in step 311, the "A" or "V" IC-ECG oscillating signal segment data passed from the filtering step 310, is processed using a time sequence classification process. In step 311, the IC-A annotations (or IC-V annotations) for all of the IC-ECG channels relative to a sensed heart beat are compared to one or more pre-determined templates. In lieu of selecting either "A" or "V" IC-ECG data, annotations from both could be used in a comparison step against an IC-A/IC-V combination template.

Figure 3C:
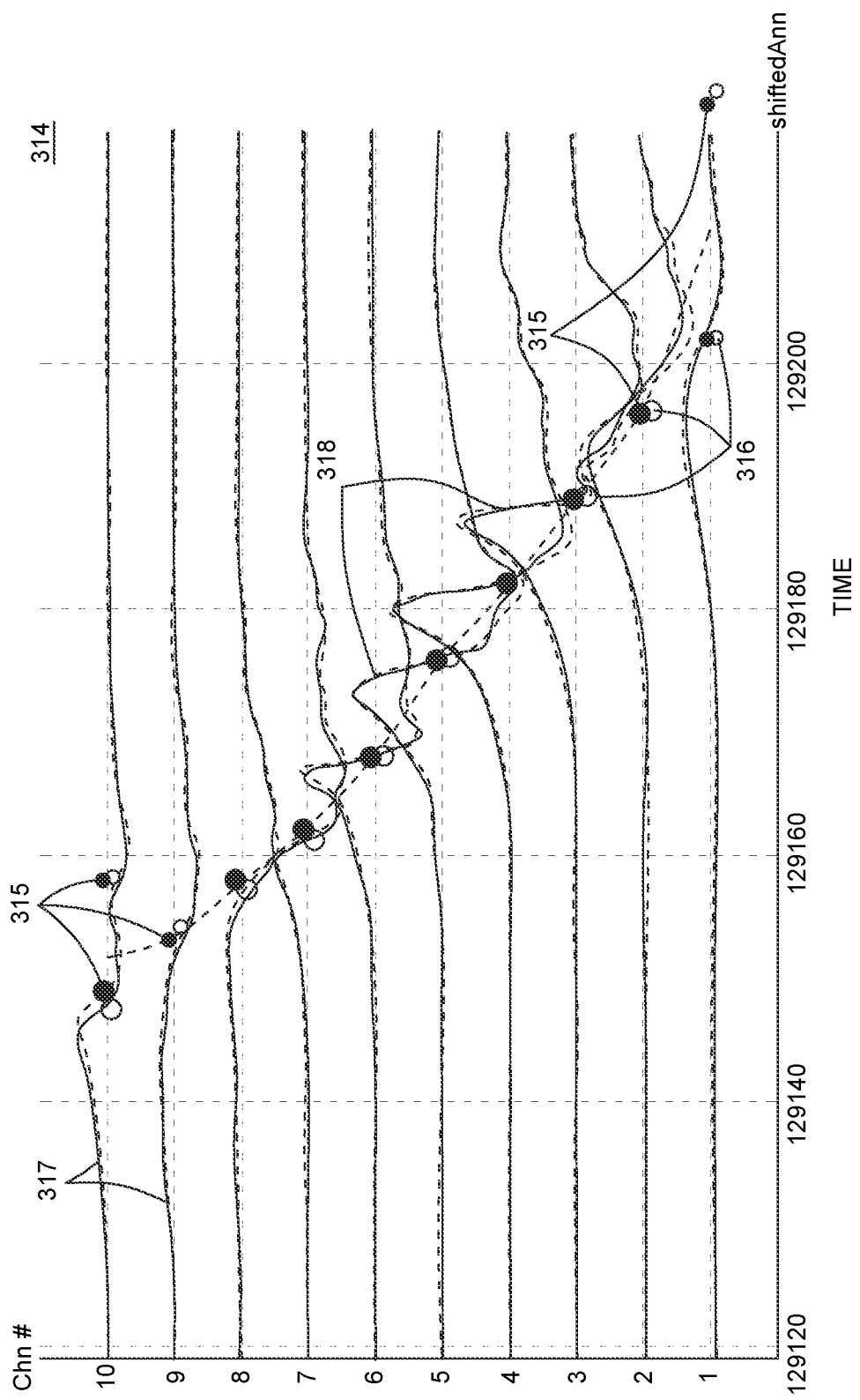
FIG. 3C is an example ECG time sequence comparison displaying good similarity.
Figure 3D:
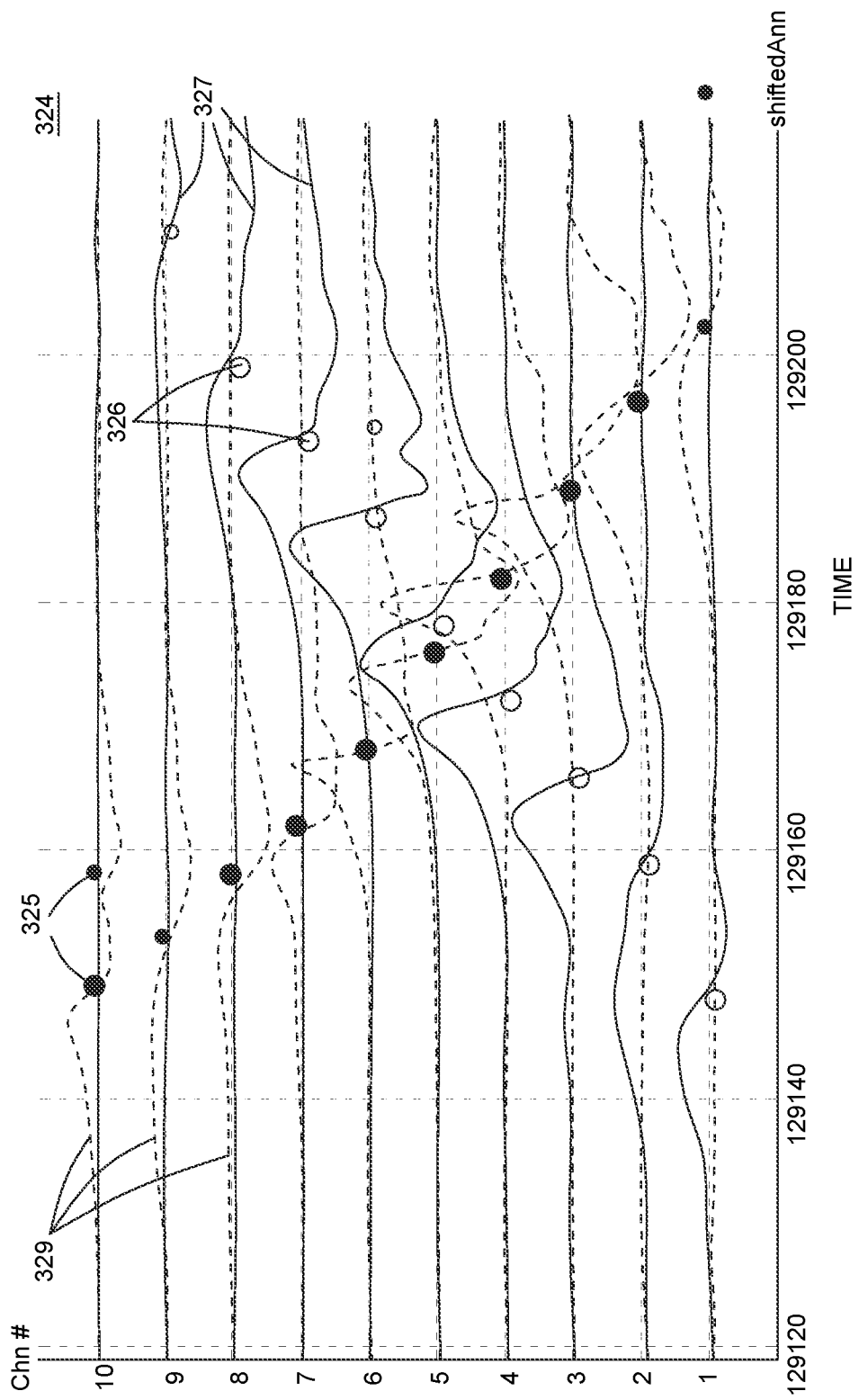
FIG. 3D is an example ECG time sequence comparison displaying poor similarity.

FIGS. 3C and 3D show schematic views of two time sequence comparisons with the same template of IC-ECG oscillating signal segment data with respect to two different sensed heartbeats per step 311 of FIG. 3B.

FIG. 3C is an example time sequence comparison graph 314 displaying good similarity between template annotations (black points) 315 of template ECG channel traces 317 (dashed lines) and the annotations (white points) 316 of the IC-ECG oscillating signal traces 318 (solid lines) of data with respect to a first sensed heartbeat. A dotted trend line is shown connecting the template annotations 315.

FIG. 3D is a second example time sequence comparison graph 324 displaying bad similarity between the same template annotations (black points) 325 of template ECG channel traces 329 (dashed lines) and the annotations (white points) 326 of the IC-ECG oscillating signal traces 327 (solid lines) of data with respect to a second different sensed heartbeat. Here, the template annotations 325 and template ECG channel traces 329 are identical to the template annotations 315 and template ECG channel traces 317 of FIG. 3C.

To determine similarity or dissimilarity of "A" IC-ECG oscillating signal segment data of a sensed heartbeat with the template annotations of an Atrial time sequence template, the processor 14 can be configured to perform an Atrial time sequence comparison of IC-A annotations reflective of the sensed heartbeat with the Atrial template annotations by calculating a time value difference between the IC annotation time value of the IC-A annotation for each channel of the sensed heartbeat and a respective template channel annotation time value. The predetermined degree of Atrial time sequence similarity can then be determined to occur when the combination of the absolute value of the combined differences is no greater than a selected A-time threshold.

To determine similarity or dissimilarity of "V" IC-ECG oscillating signal segment data of a sensed heartbeat with the template annotations of a Ventricular time sequence template, the processor 14 can be configured to perform a Ventricular time sequence comparison of IC-V annotations reflective of the sensed heartbeat with the Ventricular template annotations by calculating a time value difference between the IC annotation time value of the IC-V annotation for each channel of the sensed heartbeat and a respective template channel annotation time value. The predetermined degree of Ventricular time sequence similarity can then be determined to occur when the combination of the absolute value of the combined differences is no greater than a selected A-time threshold.

Alternative methods of determining similarity may be implemented that include, but are not limited to, sum of absolute differences, route mean squares, weighted values of same or Minkowski distance comparison.

Initial Atrial time sequence and Ventricular time sequence templates can be based on respective "A" and "V" IC-ECG oscillating signal segment data of a normal heartbeat or averages of a series of normal heartbeats of the subject. New templates can be generated by the processor from "A" or "V" IC-ECG oscillating signal segment data based upon a condition that a heartbeat classification is not made based on a respective comparison to existing morphology, Atria time sequence or Ventricle time sequence templates for that data. For example, the annotations (white points) 326 of the IC-ECG oscillating signal traces 327 (solid lines) of data with respect to the second different sensed heartbeat illustrated in FIG. 3D could be used as a basis of a new second template for comparison to IC-ECG signals of subsequent sensed heartbeats.

Figure 4:
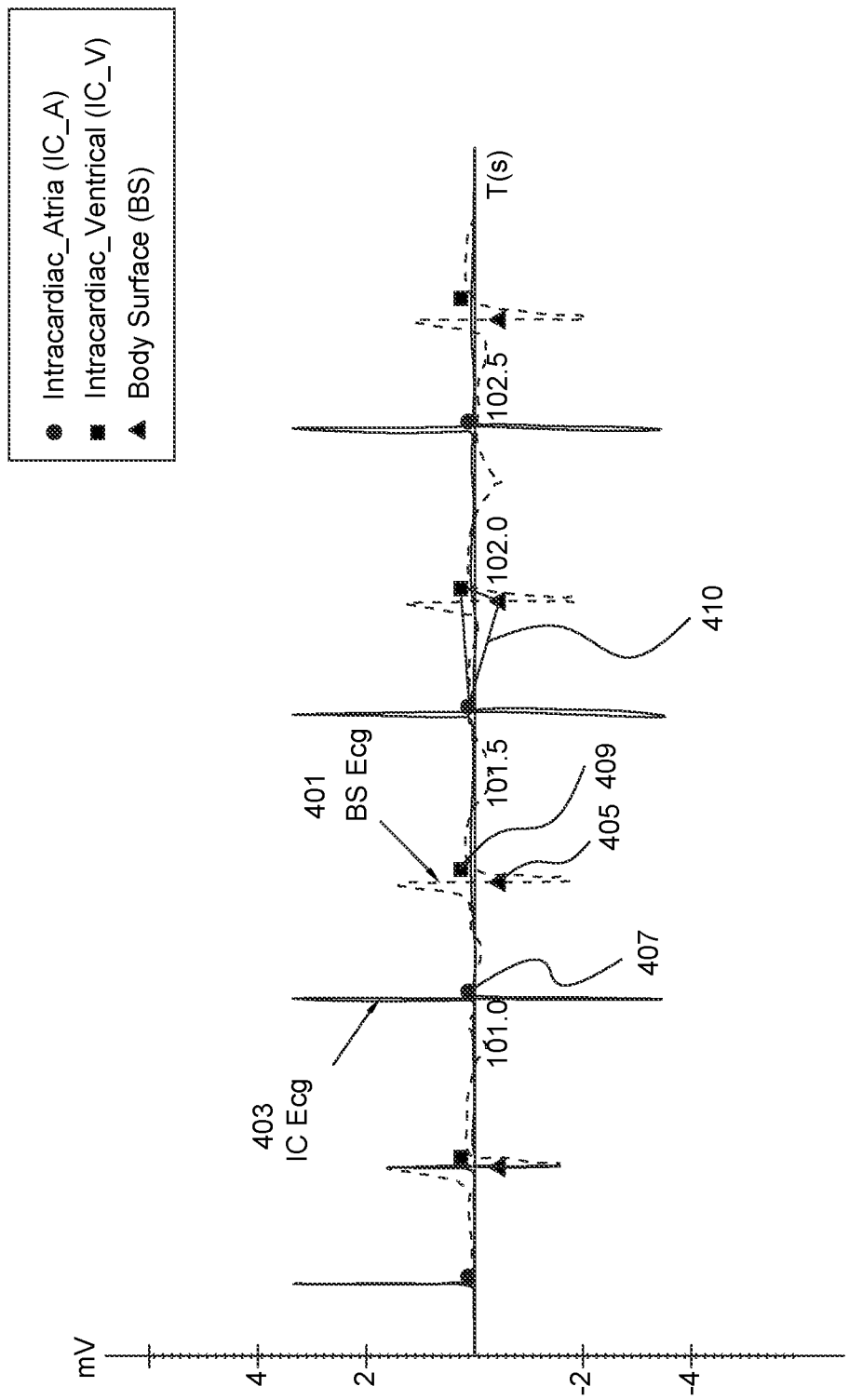
FIG. 4 is a graphic illustration of ECG signals of sensed heartbeats where a representative body source (BS) trace from BS electrodes is overlaid on an intracardiac (IC) trace from an IC electrode of the same sensed heartbeats with annotation references noted.
Figure 6:
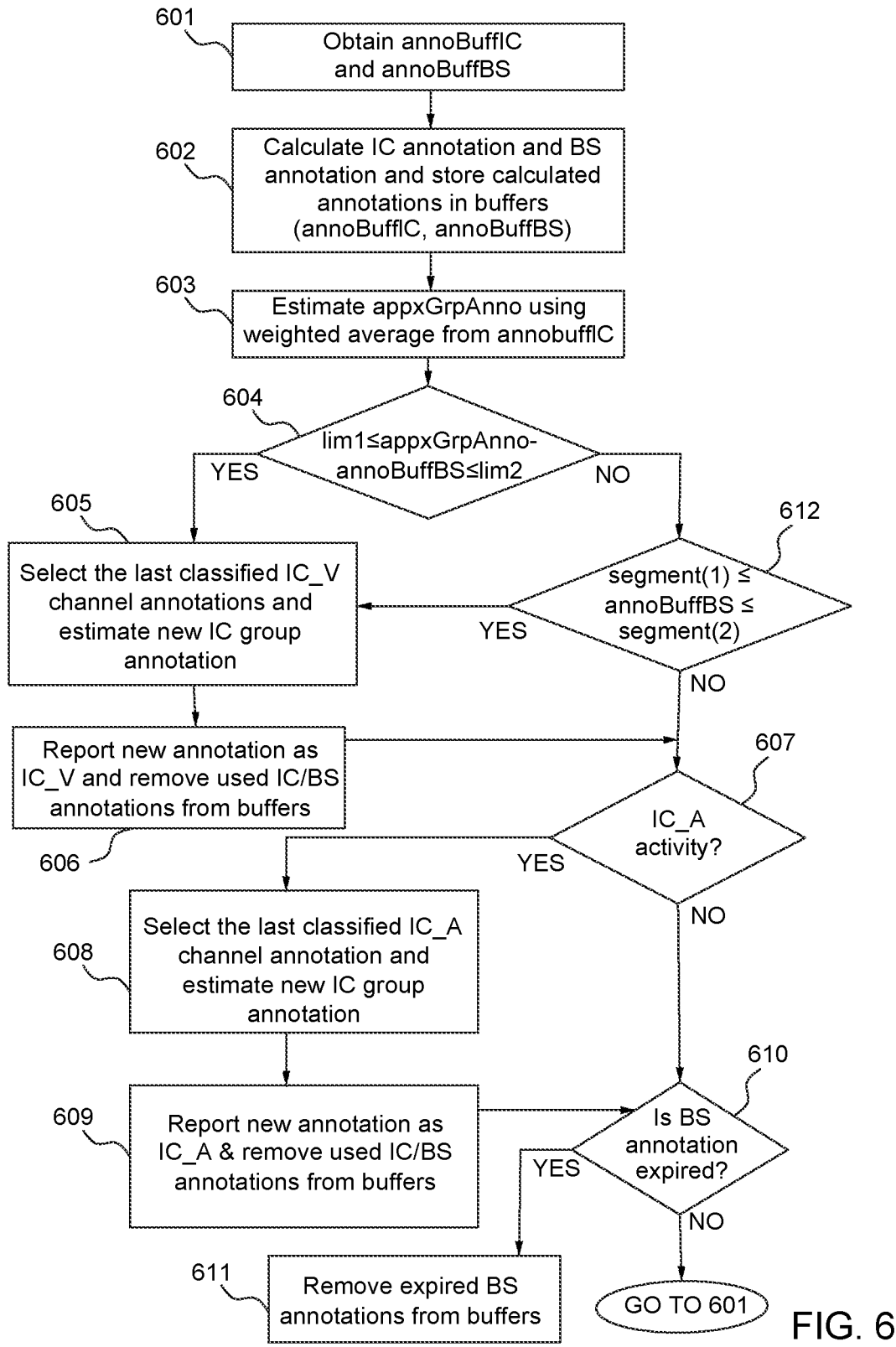
FIG. 6 is an expanded flow diagram of the time based example of the A-V discrimination step FIG. 3B.

FIGS. 4-6 illustrate a time sequence technique for A/V differentiation using IC-ECG oscillating signal segment annotations. FIG. 4 is a graphic illustration of ECG signals of a series of four sensed heartbeats where a representative body source (BS) trace 401 from BS electrodes 13 is overlaid on an intracardiac (IC) trace 403 from an IC electrode 11 of the same series of sensed heartbeats. Annotations of the oscillating signal segments are illustrated. Note that a point representing any specific component of the reference ECG may be used as the reference annotation. By none limiting way of example, such components can include maximum (peak positive) deflection of heart beat, minimum (peak negative) deflection of heart beat, maximum upslope (dV/dT), maximum downslope and/or energy center of the complete heartbeat. The choice of specific point or some integrative position (such as energy center) depends on the method used to perform the analysis.

The time values of BS annotations (triangles) 405 of BS oscillating signal segments general fall between respective IC-A annotations (circles) 407 and IC-V annotations (squares) 409 of IC oscillating signal segments for a given sensed heartbeat. This results in a classic triangular relationship 410 of the BS, IC-A and IC-B annotations for a given sensed heartbeat. These characteristics of normal hearty activity are explained in further detail in U.S. Pat. No. 9,259,165.

FIG. 5 further illustrates these characteristics for a single sensed heartbeat. As illustrated in FIG. 5, traces 501 of BS-ECG signals each characteristically reflect a single oscillating signal segment for the sensed heartbeat. Separately presented is trace 503 of the one IC-ECG signal channel that characteristically reflects two oscillating signal segments for the sensed heartbeat; the first 505 corresponding to atrial activation activity (IC-A segment) and the second 507 corresponding to ventricular activation activity (IC-V segment). For illustrative purposes, a collective BS annotation 511 is provided on the graph of the IC ECG trace along with the IC-A annotation 515 and IC-V annotation 507 of the respective IC oscillating signal segments.

In order to determine whether a particular IC oscillating signal segment represents atrial activation activity or ventricular activation activity, a comparison of the time value of the annotation of the IC oscillating signal segment with the time value of the annotation of the BS signal segments for the sensed heartbeat. The inventors have recognized the generally the IC-V type annotations are much closer in time value to the time values of respective BS annotations than are the time values of IC-A type annotations. Although usually, a BS annotation occurs before a respective IC-V annotation as described for example in U.S. Pat. No. 9,259,165, the inventors have recognized that this may not always be the case. Accordingly, a time sequence A/V differentiation technique is provided based on a comparison of IC annotation time values to a range within which time values of respective BS annotations fall.

In implementation, to perform step 309 of FIG. 3B, the processor 14 is configured to discriminate IC-ECG signal oscillating signal segments as A-activity or V-activity such that an IC-ECG oscillating signal segment is designated as V-activity upon a condition that the IC annotation time value relative to the sensed heartbeat is within a range of time values starting a predetermined amount before the BS annotation time value relative to the sensed heartbeat and ending a predetermined amount after the BS annotation time value relative to the sensed heartbeat and to otherwise designate the IC-ECG oscillating signal segment as A-activity. Generally, for a IC-ECG signal oscillating signal segments to be classified as V-activity, the IC annotation must between two limits "lim1" and "lim2" bracketing the BS annotation 511 as illustrated in FIG. 5. This is in fact the case for the illustrated IC annotation 517 which is an IC-V annotation. If the IC annotation does not fill within the range defines by "lim1" and "lim2," it is classified as directed to atrial activity by default. In one embodiment, the limit values are set along the X-axis (time) at about 20 ms for lim1 and 80 ms for lim2.

FIG. 6 is an example flow diagram of this time sequence method of discrimination between IC-A and IC-V activities based on BS annotations. As indicate in the flow diagram, the method computes the weighted average of the channel annotations (from an IC annotation buffer annoBuffIC) and compares the obtained value (appxGrpAnno) with BS annotations contained in a corresponding buffer (annoBuffBS). If the difference appxGrpAnno-annoBuffBS falls within the boundaries, e.g., {lim1,lim2} which can have default values of −20 ms, 80 ms, the method calculates the group annotation and reports the new IC annotation as IC_V type. To calculate the group annotation value, the method uses the last previous classified IC_V annotation results. If the condition is not met, the method checks an additional condition: are there any detected BS annotations within the limits of the current IC segment? If this condition is true, then the method calculates the group annotation and reports the new IC annotation as IC_V type. Otherwise as well as after the IC_V annotation calculation, the method starts checking for IC_A activity presence.

The condition of IC_A activity presence is a set of rules that checks the following:

Is given appxGrpAnno located before the current data buffer (too much time passed)?

is given appxGrpAnno checked when a later IC_V activity has been classified before?

Is given appxGrpAnno older than last BS annotation (from annoBuffBS)?

If one of these conditions is true, the analyzed activity is classified as IC_A. The method calculates the group annotation and reports the new IC annotation as IC_A type. If none of the conditions is true, the method proceeds to the next step.

The last step of the method is to clean up the BS annotation buffer, if it contains expired BS annotations.

The method may use the inter activation time as a template that is matched with any other heartbeat in the accumulated data. The method may also include processes to handle "miss of activation", that is, activations that are missed or skipped in some of the channels as some signals may become very small during the medical procedure, e.g., due to minimal patient respiration.

Accordingly, the present method can recognize the difference, e.g., can differentiate, as heartbeat changes mode.

FIG. 6 shows the following steps:

Step 601: Obtain annoBuffIC and annoBuffBS.

Step 602: Calculate IC annotation and BS annotation, typically in real time. The IC annotations may be calculated per channel. These calculated annotations are stored in buffers, e.g., IC annotation buffer (annoBuffIC) and BS annotation buffer (annoBuffBS).

Step 603: Estimate appxGrpAnno by computing weighted average of IC channel annotations using annoBuffIC.

Step 604: Determine whether lim1<appxGrpAnno<lim2. If appxGrpAnno is between lim1 and lim2 (604=YES), then Step 605, select the last classified IC_V channel annotations and estimate new IC group annotation (GrpAnno)

Step 606: report new annotation as IC_V and remove used IC/BS annotations from buffers.

Step 607: Determine whether there is additional IC_A activity. If there is additional activity (607=YES), in step 608, select the last classified IC_A channel annotations and estimate new IC group annotation.

Step 609: Report new annotation as IC_A and remove used IC/BS annotations from buffers. Continue at step 610.

If no additional activity is detected (607=NO), continue at step 610.

Step 610: Determine whether BS annotation is expired. If the BS annotation is expired (610=YES), at step 611, remove expired BS annotations from buffers. Continue at step 601.

If BS annotation is not expired (610=NO), continue at step 601.

If the apprxGrpAnno is not between lim1 and lim2 (604=NO), at step 612, then determine whether annoBuffBS is between segment(1) and segment(2) [segment(1)<=annoBuffBS<=segment(2)]. If annoBuffBS is between these two limits, then go to step 605. If annoBuffBS is not between these two limits, then go to step 607.

Figure 7:
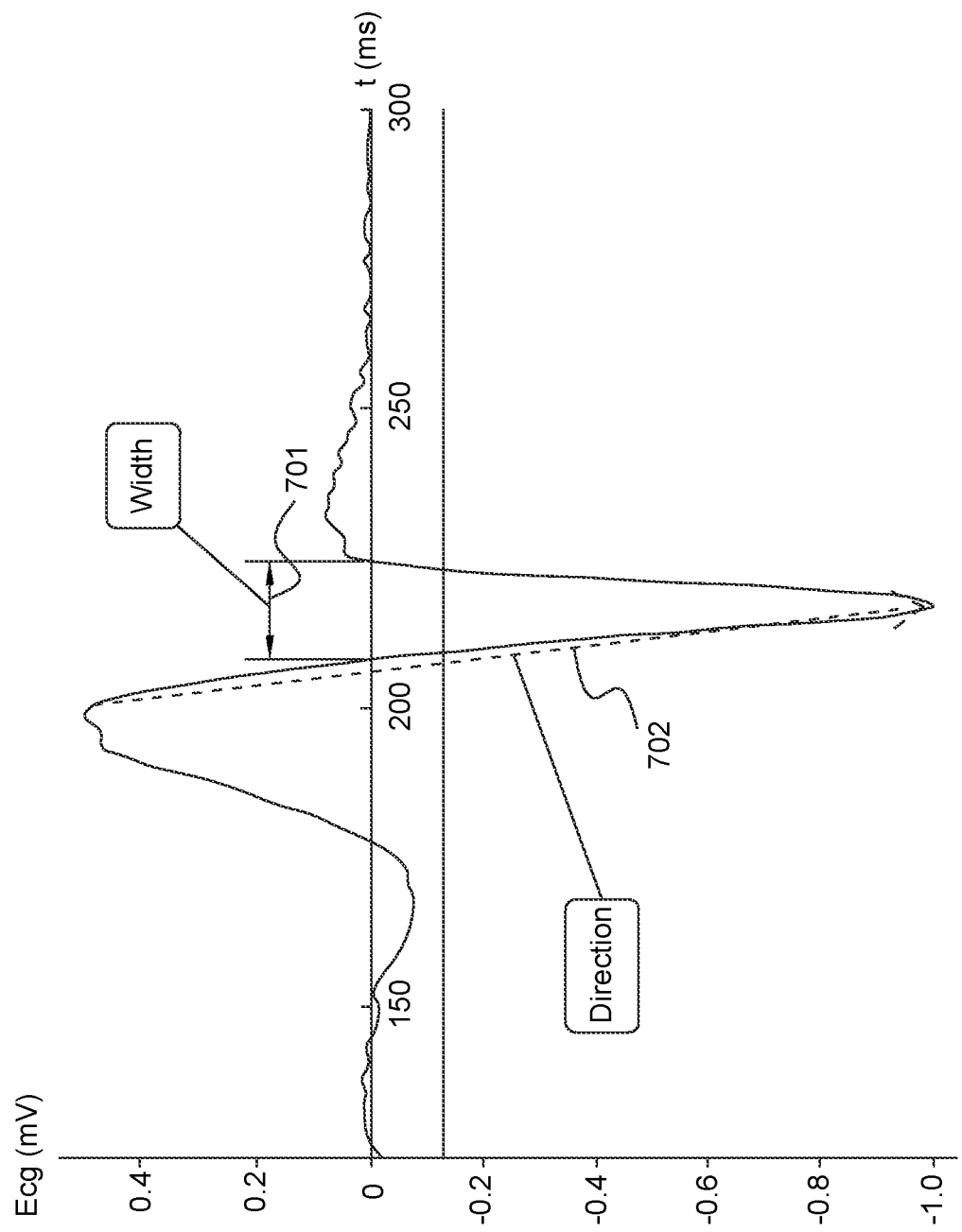
FIG. 7 is a graphic illustration of an ECG oscillating signal segment usable as the basis of a morphology based example of A-V discrimination step FIG. 3B.
Figure 8:
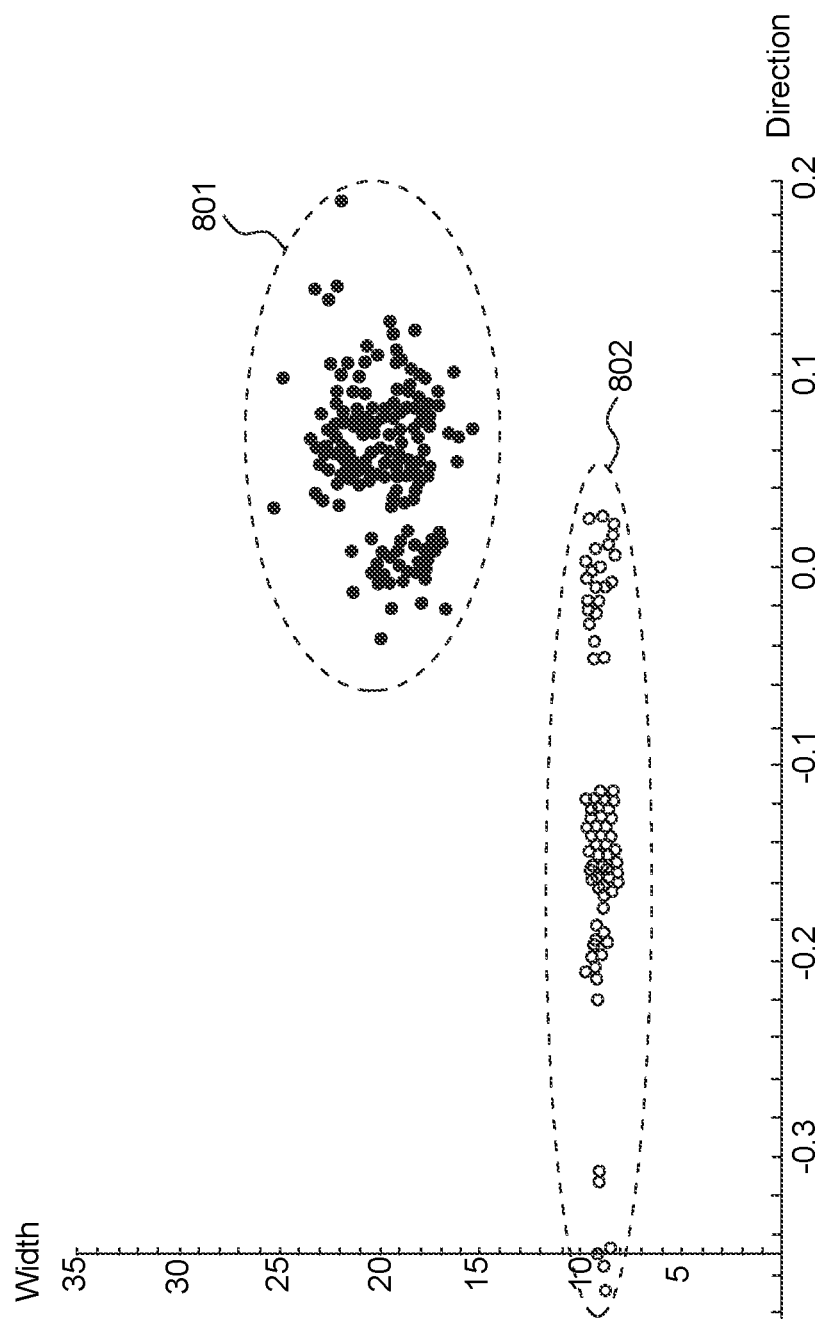
FIG. 8 is a graphic illustration of clusters of A-activity and V-activity using the morphology example of A-V discrimination step FIG. 3B.
Figure 9:
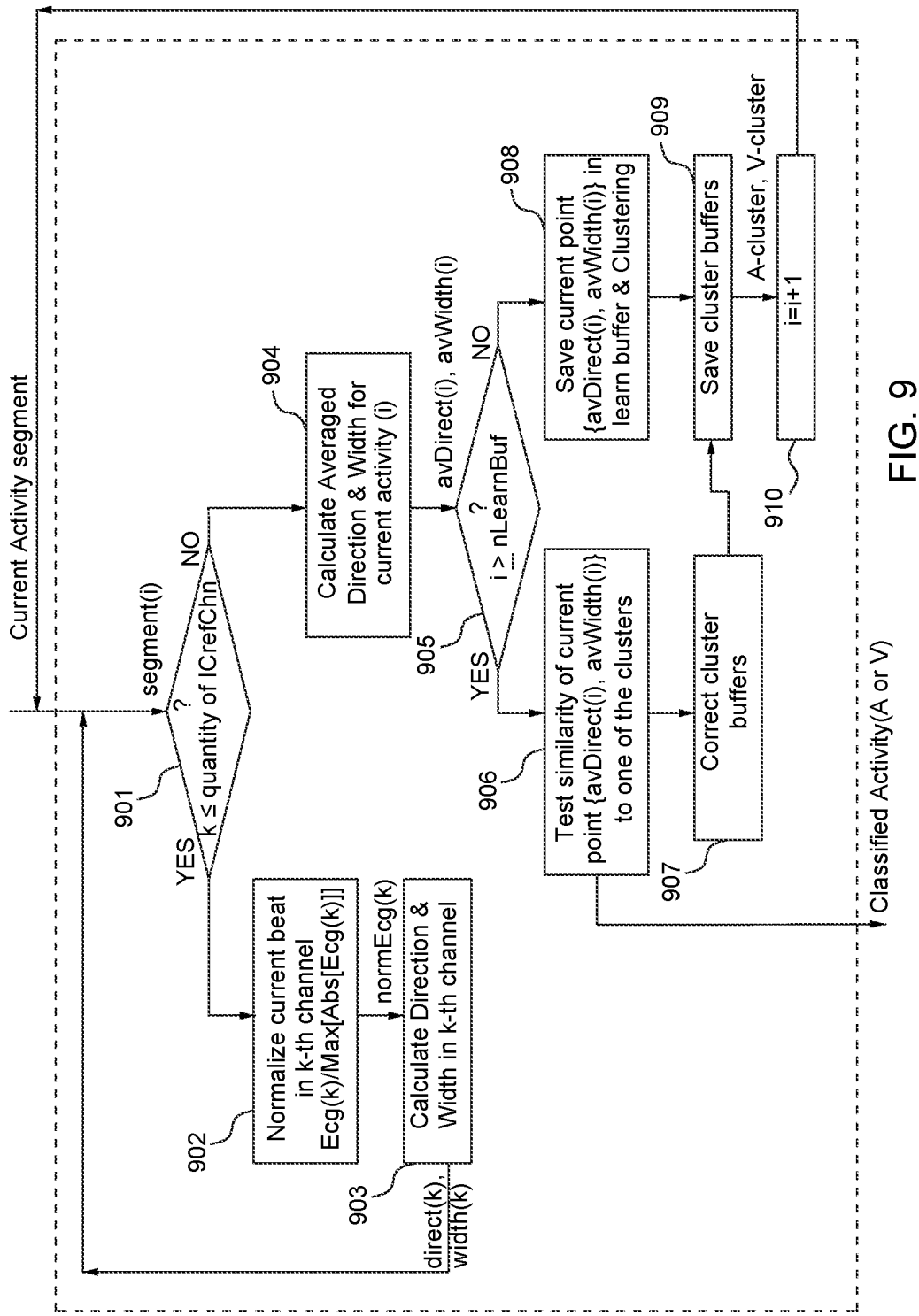
FIG. 9 is a flow diagram of the morphology based example of A-V discrimination step FIG. 3B.

FIGS. 7-9 illustrate a morphological technique for A-V discrimination using the IC-ECG oscillating signal segment morphological (shape) features. For implementation, processor 14 is configured to discriminate IC-ECG oscillating signal segments as A-activity or V-activity such that an IC-ECG oscillating signal segment is designated as A-activity or V-activity based upon morphology characteristics of the IC-ECG oscillating signal segment.

In one embodiment, two characteristics may be used as morphology characteristics of the heartbeat. One characteristic is the slope (direction) of the line connecting "peak-to-peak" (MAX-MIN) points of the heartbeat. Another characteristic is the width of the heartbeat main peak at a certain level.

FIG. 7 illustrates direction and width parameter definitions for morphological features. Both the width 701 between main peaks at a certain level and the direction of the slope 702 are illustrated. The direction parameter 702 may be used as a morphological feature because A-activities and V-activities originate from different sources and therefore have different arrival directions. The width parameter 701 shows that the V-activity ECG relative to the A-activity ECG contains more low-frequency components. Because it is reasonable to expect that the value of the width parameter 701 for the V-activity will be higher than for the A-activity, the width parameter 701 is another morphological feature of interest.

FIG. 8 illustrates results of classifying A-activities and V-activities of the intracardiac ECG. As shown in FIG. 8, two point groups 801, 802 are clearly separated in Direction- Width coordinates. The upper group 801, which has a smaller spread of its members (in direction), is related to V-activity.

FIG. 9 is a flow diagram of the classification method based on the morphologic parameters. For a given activity interval (segment(i)), a normalization is performed for every channel of IC reference ECGs (ECG(k)). Then the method calculates the direction (direct(k)) and width (width(k)) parameters for normalized heartbeats (normEcg(k)). The direction parameter is determined by the following formula:

direct(k)=arcTan[(yMax(k)−yMin(k))/(xMax(k)−xMin(k))], where:

arcTan[ . . . ]—arctangent function;
{xMax(k),yMax(k)}—coordinates of maximum of the normalized heart beat for k-th channel;
{xMin(k),yMin(k)}—coordinates of minimum of the normalized heart beat for k-th channel.

The next step is computing the averaged values of the found parameters (avDirect(i), avWidth(i)) for given segment(i).

Until the learning buffer reaches the required number of points, each point is saved and clustering is performed on the points in the buffer. FIG. 8 shows the dual parameter clustering, where the element (point) of groups is described by two parameters ({avDirect(i), avWidth(i)}). Any known method such as K-mean may be used as the clustering method. After clustering, the method saves two separated groups (A-cluster & V-cluster) for later use. Once the learning buffer is full, the method tests a similarity of each incoming point to the clusters. The test answer is reported. The method makes refinement operations for the clusters such as outlier deleting, a cluster center correcting, etc.

The steps for the method shown in FIG. 9 are as follows. In step 901, begin the current activity segment. Determine whether k<=quantityOfICrefChn. If k<=quantityOfICrefChn (901=YES), then, in step 902, calculate normEcg(k) to normalize current beat in k-th channel, that is: normEcg(k)=Ecg(k)/Max[Abs[Ecg(k))].

In step 903, calculate direction and width in k-th channel and continue processing at step 901.

If k>quantityOfICrefChn (901=NO), then in step 904, calculate avDirect(i), avWidth(i) as averaged direction and width for current activity (i).

In step 905, determine whether or not I>=nLearnBuf. If I>=nLearnBuf (905=YES), then, in step 906, test similarity of current point (avDirect(i), avWidth(i)) to one of the clusters. In step 907, correct cluster buffers and continue processing at step 909.

If I<nLearnBuf (905=NO), in step 908, save the current point (avDirect(i), avWidth(i)) in learn buffer and clustering. In step 909, save cluster buffers. In step 910, increment the A-cluster and V-cluster by setting i=i+1.

In implementing the morphological A-V discrimination method, the processor 14 is configured to discriminate IC-ECG oscillating signal segments as A-activity or V-activity such that an IC-ECG oscillating signal segment is designated as V-activity upon a condition that a combination of a slope and a width of a primary oscillation is less than a predetermined threshold and to otherwise designate the IC-ECG oscillating signal segment as A-activity.

Figure 10:
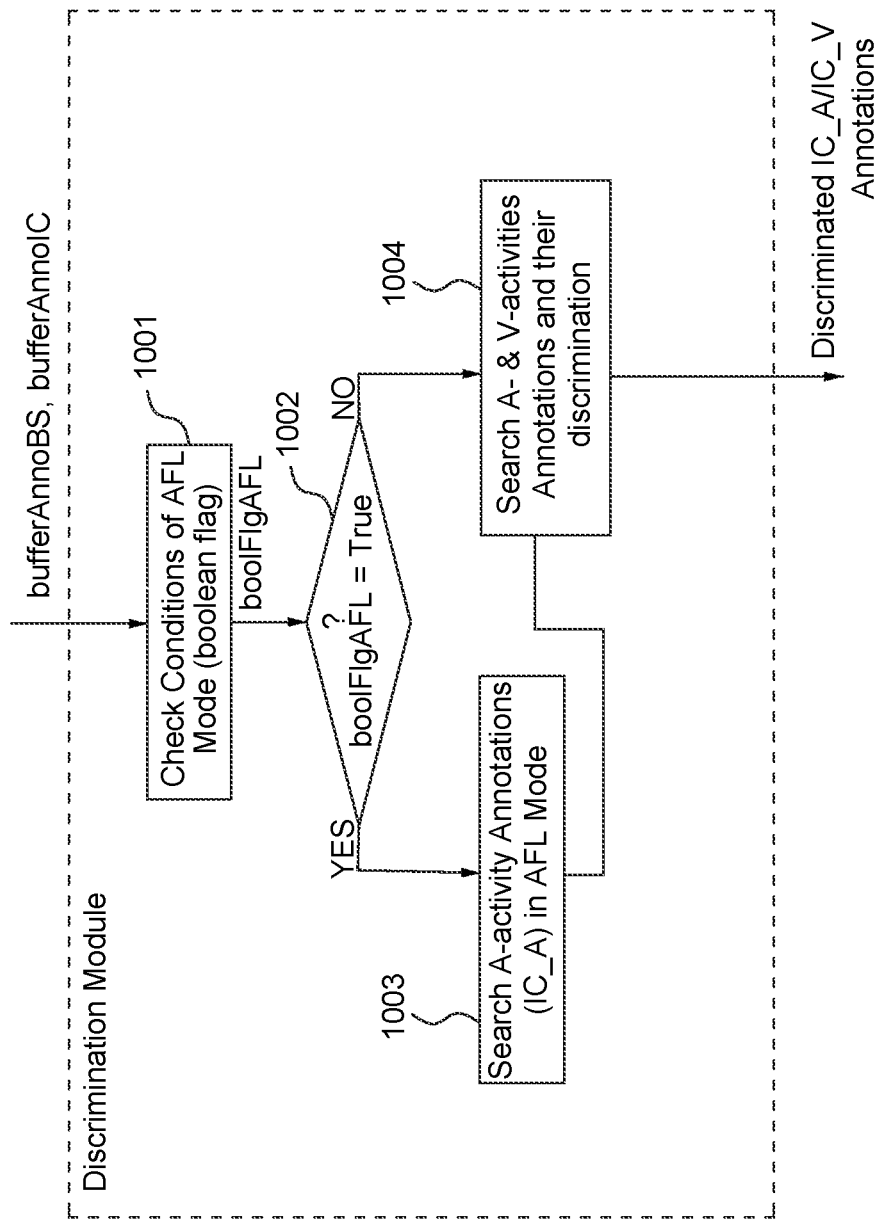
FIG. 10 is a flow diagram of an atrial flutter (AFL) mode method in an embodiment of the present invention.

FIGS. 10-12A-D illustrate a modification to the system for the arrhythmia case of atrial flutter (AFL). In AFL, A-activities often occur around the same time as the BS annotations. As a result, the classification can be incorrect, that is, A-activity can be misclassified as V-activity. In this embodiment, an AFL mode method is presented, as shown in FIG. 10. The method of FIG. 10 is combined with the method discussed in FIG. 3B, above. FIG. 10 contains two sub-blocks. The first sub-block is designed for searching A-activity under Atrial Flutter (AFL) which is explained further in connection with FIG. 11.

AFL is an abnormal heart rhythm that can cause the top chambers (atria) and the bottom chambers (ventricles) to beat at different speeds. It is one of the most common cardiac arrhythmias. It is important to note that A- and V-activities may overlap one another under AFL, so this situation may be processed by special methods. Firstly, the AFL mode conditions are checked; if their combination is true, AFL sub-block starts its action, otherwise the second sub-block starts the discrimination process. For the second sub-block, two alternative embodiments are presented: based on BS annotations (shown in FIG. 6) and based on morphological features of IC ECG (shown in FIGS. 7-9). The second embodiment is useful in a case in which BS ECGs cannot be used.

The steps in FIG. 10 are as follows. In step 1001, the block of the AFL mode checks flutter conditions and the check results in a Boolean flag (boolFlgCL). Step 1002 determines whether or not boolFlgCL is true. If boolFlgCL is true (1002=YES), in step 1003, the atrial annotations are searched. In particular, in step 1003, the classifier initiates the block of the flutter mode (as discussed in FIG. 11, below) and then the block of the blanking window classification method (as discussed in FIG. 3, above).

If boolFlgCL is not true (1002=NO), the block of the blanking window method is activated, 1004, which is equivalent to the algorithm disclosed in FIG. 6, as discussed above.

The main conditions to enter AFL (flutter mode) may be: fast rhythm (CL, 450 ms); high stability of the CL (relative standard deviation approximately 5-7%) and the ratio of annotations quantity for IC to BS is greater than 1. In order to calculate these characteristics, the method uses the updating buffers of the last classified A-activity IC annotations (bufferAnnoA) and the last estimations of all annotation candidates before classification (bufferAnnoAV).

Figure 11:
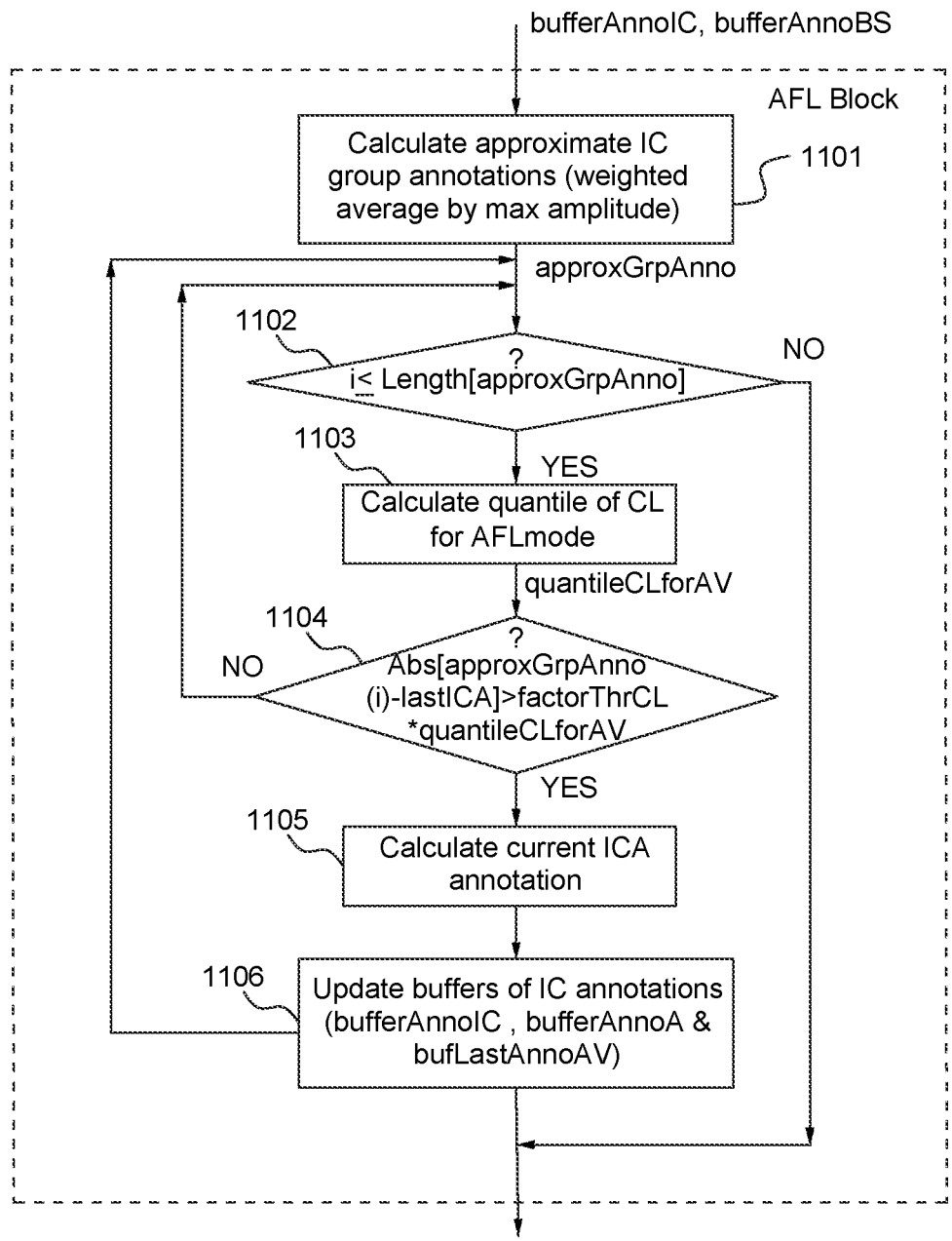
FIG. 11 is an expanded flow diagram of a portion of the AFL mode method of FIG. 10.

FIG. 11 shows an AFL mode method for block 1003 of FIG. 10. This method uses and updates bufferAnnoA, bufferAnnoAV global buffers and temporal buffer of the IC channel annotations (bufferAnnoIC). The method starts from calculation of an approximate group annotation (approxGrpAnno) which is the weighted average of all found channel annotations:

$$approxGrpAnno = \frac{\sum_k A(k) * annChnIC(k)}{\sum_k A(k)},$$

where:

where:

annChnIC(k)—IC annotation in k-th channel;
A(k)—Ecg maximal absolute value of k-th channel.

Next the block performs the calculations, condition validity and IC_A estimation in a loop. A quantity of the loop steps depends on the element number of approxGrpAnno vector. The loop step starts from calculating the CL quantile (quantileCLforAV) for current state of bufferAnnoAV. Then the method checks the following condition:

approxGrpAnno(i)−bufferAnnoA(−1)>
factorThrCL*quantileCLforAV, where:
approxGrpAnno(i)—value of approxGrpAnno in i-th loop step;
bufAnnoA(−1)—the last classified IC_A annotation;
factorThrCL—some pre-set factor for the lower bound of CL.

If the condition is true, we can estimate IC_A annotation, otherwise the loop starts a next step. After a successful IC_A annotation estimation, its value is saved in bufAnnoA buffer and first buffer element is deleted. The same update is carried out for bufLastAnnoA V buffer. The used element of bufferAnnoIC buffer is deleted.

The steps of the method shown in FIG. 11 are as follows. In step 1101, calculate approximate IC group annotations, e.g., weighted average by max amplitude. In step 1102, determine whether or not I<=Length[approxGrpAnno]. If I<=Length[approxGrpAnno (1102=YES), then in step 1103 calculate quantile of CL for AFL mode.

In step 1104, determine whether or not Abs[approxGrpAnno(i)−lastICA]>factorThrCL*quantileCLforAV. If Abs [approxGrpAnno(i)−lastICA]>factorThrCL* quantileCLforAV (1104=YES), then in step 1105, calculate current ICA annotation. In step 1106, update buffers of IC annotations (e.g., bufferAnnoIC, bufferAnnoA and BufLastAnnoAV).

If Abs[approxGrpAnno(i)−lastICA]<= factorThrCL*quantileCLforAV (1104=NO), then go to step 1102.

If I>Length[approxGrpAnno] (1102=NO), then processing is complete.

A results comparison of classification methods with AFL mode module 1202 and without AFL mode module 1201 for atrial flutter case is presented in FIGS. 12D and 12C, respectively. As shown, a classifier without the AFL mode module misses each second A-activity. For general implementation of the AFL mode, the processor 14 is configured to designate the IC-ECG oscillating signal segments as A-activity upon the condition that atrial flutter is detected for the sensed heartbeat and a blanking window exists between successive IC-ECG oscillating signal segments for the sensed heartbeat.

The present method may have two modes: Manual mode and Automatic ("auto") mode. In either mode, one can provide a beat to track and/or can set thresholds around time to filter out a beat.

In auto mode, one can look at all beats acquired in statistical manner and cluster the beats by time sequence. The cluster may be presented to the physician as a filtered collection of data; the extracted cluster of beats can be used to generate the map. In the auto mode, there is no need to provide a template; instead, the present method generates a template from the acquired beats.

In manual mode, the user may select data of a specific heartbeat for the basis of a time sequence template. Then, the method takes that time sequence template and uses it to match all the heartbeats in the acquired data. Only heartbeats that are matched are used in the LAT map.

It will be appreciated by persons skilled in the art that the present teachings are not limited to what has been particularly shown and described hereinabove. Rather, the scope of the present teachings include both combinations and subcombinations of the various features described hereinabove, as well as variations and modifications thereof that are not in the prior art, which would occur to persons skilled in the art upon reading the foregoing description.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be mask works that are then used in a semiconductor manufacturing process to manufacture a processor which implements methods described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A medical apparatus configured to classify heartbeats based on intracardiac and body surface electrocardiogram (ECG) signals comprising:

an intracardiac catheter configured to obtain multiple channels of intracardiac ECG (IC-ECG) signals via respective multiple electrodes when disposed within a heart within a body of a subject;

body surface ECG sensors configured to obtain multiple channels of body surface ECG (BS-ECG) signals via multiple electrodes when disposed on the body of the subject;

a processor configured to receive and process respective ECG signals from the intracardiac catheter and body surface ECG sensing device;

the processor configured to define a BS annotation of BS-ECG oscillating signal segments reflective of a sensed heartbeat of the subject, the BS annotation including a BS annotation time value relative to the sensed heartbeat;

the processor configured to perform a morphology comparison of the BS-ECG oscillating signal segments reflective of the sensed heartbeat with one or more morphology templates, where each morphology template is associated with a heartbeat classification of one heart chamber type, and classify the sensed heartbeat as corresponding to the associated heartbeat classification of a template for which the morphology comparison reflects a predetermined degree of morphology similarity;

the processor configured to define IC annotations of IC-ECG oscillating signal segments for each channel which reflect heart chamber activity of the sensed heartbeat of the subject, each IC annotation including an IC annotation time value relative to the sensed heartbeat;

the processor configured to discriminate IC-ECG oscillating signal segments and designate IC annotations per heart chamber type;
the processor configured to perform a time sequence comparison of IC annotations reflective of the sensed heartbeat with one or more time sequence template of the same heart chamber type, where each time sequence template is associated with a classification, and classify the sensed heartbeat as corresponding to the associated classification of a template for which the time sequence comparison reflects a predetermined degree of time sequence similarity; and
the processor configured to create a new morphology time sequence template based upon a condition that a heartbeat classification is not made based on a respective comparison to existing morphology time sequence templates.

2. The apparatus of claim 1 wherein the processor is configured to discriminate IC-ECG signal oscillating signal segments with respect to heart chamber activity as atrial activity (A-activity) or ventricle activity (V-activity) such that an IC-ECG oscillating signal segment is designated as V-activity upon a condition that the IC annotation time value relative to the sensed heartbeat is within a range of time values starting a predetermined amount before the BS annotation time value relative to the sensed heartbeat and ending a predetermined amount after the BS annotation time value relative to the sensed heartbeat and to otherwise designate the IC-ECG oscillating signal segment as A-activity.

3. The apparatus of claim 2 wherein the processor is configured to designate the IC-ECG oscillating signal segment as V-activity upon the condition that the IC annotation time value relative to the sensed heartbeat is within a range of time values starting at no less than 20 milliseconds before the BS annotation time value relative to the sensed heartbeat and ending no more than 80 milliseconds after the BS annotation time value relative to the sensed heartbeat.

4. The apparatus of claim 1 wherein the processor is configured to discriminate IC-ECG oscillating signal segments with respect to heart chamber activity per heart chamber type based upon morphology characteristics of the IC-ECG oscillating signal segment.

5. The apparatus of claim 4 wherein the processor is configured to discriminate IC-ECG oscillating signal segments with respect to heart chamber activity per heart chamber type based upon a combination of a slope and a width of a primary oscillation with respect to a predetermined threshold.

6. The apparatus of claim 1 wherein the processor is configured to designate the IC-ECG oscillating signal segments with respect to heart chamber activity per heart chamber type based upon detection of atrial flutter for the sensed heartbeat and a blanking window exists between successive IC-ECG oscillating signal segments for the sensed heartbeat.

7. The apparatus of claim 1 wherein:
the processor is configured to perform a sequence comparison of IC annotations reflective of the sensed heartbeat with a time sequence template by:
calculating a time value difference between the IC annotation time value of the IC annotation for each channel of the sensed heartbeat and a respective template channel annotation time value, and
determining that the predetermined degree of time sequence similarity occurs when the combination of the absolute value of the combined differences is no greater than a selected time threshold.

8. The apparatus of claim 1 further comprising an output device coupled to the processor configured to selectively output classifications of sensed heartbeats resulting from morphology and time sequence comparisons.

9. The apparatus of claim 8 wherein the output device comprises a monitor configured to selectively display ECG signal and heartbeat classification data of sensed heartbeats.

10. A method for classifying heartbeats based on intracardiac and body surface electrocardiogram (ECG) signals comprising:
obtaining multiple channels of intracardiac ECG (IC-ECG) signals via respective multiple electrodes from within a heart within a body of a subject;
obtaining multiple channels of body surface ECG (BS-ECG) signals from the body of the subject;
processing the IC-ECG and BS-ECG signals;
defining a BS annotation of BS-ECG oscillating signal segments reflective of a sensed heartbeat, the BS annotation including a BS annotation time value relative to the sensed heartbeat;
performing a morphology comparison of the BS-ECG oscillating signal segments reflective of the sensed heartbeat with one or more morphology templates, where each morphology template is associated with a heartbeat classification of one heart chamber type, and classifying the sensed heartbeat as corresponding to the associated heartbeat classification of a template for which the morphology comparison reflects a predetermined degree of morphology similarity;
defining IC annotations of IC-ECG oscillating signal segments for each channel which reflect heart chamber activity of the sensed heartbeat, each IC annotation including an IC annotation time value relative to the sensed heartbeat;
discriminating IC-ECG oscillating signal segments and designating IC annotations as IC annotations per heart chamber type;
performing a time sequence comparison of IC annotations reflective of the sensed heartbeat with one or more time sequence templates of the same heart chamber type, where each time sequence template is associated with an activity classification, and classifying the sensed heartbeat as corresponding to the associated activity classification of a template for which the time sequence comparison reflects a predetermined degree of time sequence similarity; and
creating a new morphology time sequence template based upon a condition that a heartbeat classification is not made based on a respective comparison to existing morphology time sequence templates.

11. The method of claim 10 wherein the discriminating IC-ECG oscillating signal segments with respect to heart chamber activity is performed such that an IC-ECG oscillating signal segment is designated as ventricle activity (V-activity) upon a condition that the IC annotation time value relative to the sensed heartbeat is within a range of time values starting a predetermined amount before the BS annotation time value relative to the sensed heartbeat and ending a predetermined amount after the BS annotation time value relative to the sensed heartbeat and otherwise the IC-ECG oscillating signal segment is designated as atrial activity (A-activity).

12. The method of claim 10 wherein the IC-ECG oscillating signal segment is designated as V-activity upon the condition that the IC annotation time value relative to the sensed heartbeat is within a range of time values starting at no less than 20 milliseconds before the BS annotation time value relative to the sensed heartbeat and ending no more than 80 milliseconds after the BS annotation time value relative to the sensed heartbeat.

13. The method of claim 10 wherein the discriminating IC-ECG oscillating signal segments with respect to heart chamber activity per heart chamber type is performed based upon morphology characteristics of the IC-ECG oscillating signal segment.

14. The method of claim 10 wherein the discriminating IC-ECG oscillating signal segments with respect to heart chamber activity per heart chamber type is based on a combination of a slope and a width of a primary oscillation with respect to a predetermined threshold.

15. The method of claim 10 wherein the designating the IC-ECG oscillating signal segments with respect to heart chamber activity per heart chamber type is based upon detection of atrial flutter is detected for the sensed heartbeat and a blanking window exists between successive IC-ECG oscillating signal segments for the sensed heartbeat.

16. The method of claim 10 wherein:
   time sequence comparison of IC annotations reflective of the sensed heartbeat with a time sequence template is performed by:
      calculating a time value difference between the IC annotation time value of the IC annotation for each channel of the sensed heartbeat and a respective template channel annotation time value, and
      determining that the predetermined degree of time sequence similarity occurs when the combination of the absolute value of the combined differences is no greater than a selected threshold.

17. The method of claim 10 further comprising selectively outputting classifications of sensed heartbeats resulting from morphology and time sequence comparisons.

18. The method of claim 17 including selectively displaying ECG signal and heartbeat classification data of sensed heartbeats.

19. A tangible non-transitory computer-readable medium in which program instructions are stored, which, when read by a processor, cause the processor to process multiple channels of intracardiac ECG (IC-ECG) signals obtained from respective multiple electrodes within a heart within a body of a subject and multiple channels of body surface ECG (BS-ECG) signals obtained from the body of the subject, including:

defining a BS annotation of BS-ECG oscillating signal segments reflective of a sensed heartbeat, the BS annotation including a BS annotation time value relative to the sensed heartbeat;

performing a morphology comparison of the BS-ECG oscillating signal segments reflective of the sensed heartbeat with one or more morphology templates, where each morphology template is associated with a heartbeat classification of one heart chamber type, and classifying the sensed heartbeat as corresponding to the associated heartbeat classification of a template for which the morphology comparison reflects a predetermined degree of morphology similarity;

defining IC annotations of IC-ECG oscillating signal segments for each channel which reflect heart chamber activity of the sensed heartbeat, each IC annotation including an IC annotation time value relative to the sensed heartbeat;

discriminating IC-ECG oscillating signal segments and designating IC annotations as IC annotations per heart chamber type;

performing a time sequence comparison of IC annotations reflective of the sensed heartbeat with one or more time sequence templates of the same heart chamber type, where each time sequence template is associated with an activity classification, and classifying the sensed heartbeat as corresponding to the associated activity classification of a template for which the time sequence comparison reflects a predetermined degree of time sequence similarity; and creating a new morphology time sequence template based upon a condition that a heartbeat classification is not made based on a respective comparison to existing morphology time sequence templates.

20. The tangible non-transitory computer-readable medium in which program instructions are stored of claim 19, which, when read by a processor, cause the processor to discriminate IC-ECG oscillating signal segments with respect to heart chamber activity per heart chamber type based upon morphology characteristics of the IC-ECG oscillating signal segment.

* * * * *

UNITED STATES PATENT AND TRADEMARK OFFICE
CERTIFICATE OF CORRECTION

PATENT NO. : 12,226,235 B2
APPLICATION NO. : 17/712439
DATED : February 18, 2025
INVENTOR(S) : Vladimir Rubinstein et al.

It is certified that error appears in the above-identified patent and that said Letters Patent is hereby corrected as shown below:

On the Title Page

Item (56), under "OTHER PUBLICATIONS", in Column 2, Line 1, delete "Commerical" and insert -- Commercial --, therefor.

In the Specification

In Column 1, Line 11, delete "2018," and insert -- 2018, now U.S. Pat. No. 11,389,116, --, therefor.

In Column 3, Line 52, delete "invention;" and insert -- invention. --, therefor.

In Column 3, Line 57, delete "IntraCardiac" and insert -- Intracardiac --, therefor.

In Column 4, Line 31, delete "dysfunction" and insert -- dysfunction. --, therefor.

In Column 7, Line 44, delete "Deflcable" and insert -- Deficable --, therefor.

In Column 10, Line 15, delete "the" and insert -- then --, therefor.

In Column 10, Line 43, delete "though" and insert -- through --, therefor.

In Column 10, Line 56, delete "annotations," and insert -- annotations. --, therefor.

In Column 12, Line 57, delete "the" and insert -- that --, therefor.

In Column 13, Line 47, delete "is" and insert -- Is --, therefor.

In Column 14, Line 14, delete "(GrpAnno)" and insert -- (GrpAnno). --, therefor.

In Column 15, Line 40, delete "normEcg(k)=Ecg(k)/Max[Abs[Ecg(k))]." and insert

Signed and Sealed this
Twenty-second Day of April, 2025

Coke Morgan Stewart
*Acting Director of the United States Patent and Trademark Office*

CERTIFICATE OF CORRECTION (continued)
U.S. Pat. No. 12,226,235 B2

-- normEcg(k)=Ecg(k)/Max[Abs[Ecg(k))]]. --, therefor.

In Column 17, Line 16, delete "bufLastAnnoA V" and insert -- bufLastAnnoAV --, therefor.

In Column 17, Line 22, delete "I<=Length[approxGrpAnno" and insert
-- I<=Length[approxGrpAnno] --, therefor.